United States Patent [19]
Treichler et al.

[11] Patent Number: 6,103,515
[45] Date of Patent: Aug. 15, 2000

[54] PRODUCTION OF POLYPEPTIDES BY USE OF NOVEL PROTEASE DEFICIENT YEAST STRAINS

[75] Inventors: Hansjörg Treichler, Kanerkinden; Kenji Takabayashi, Basel, both of Switzerland; Dieter Heinrich Wolf, Gundelfingen, Germany; Jutta Heim, Ramlinsburg, Switzerland

[73] Assignees: Novartis Corporation, New York, N.Y.; UCP Gen-Pharma AG, Kirchberg, Switzerland

[21] Appl. No.: 07/895,581

[22] Filed: Jun. 8, 1992

Related U.S. Application Data

[63] Continuation of application No. 07/346,670, May 3, 1989, abandoned.

[30] Foreign Application Priority Data

| May 4, 1988 | [GB] | United Kingdom | .................. 8810524 |
| May 27, 1988 | [GB] | United Kingdom | .................. 8812627 |
| Mar. 29, 1989 | [GB] | United Kingdom | .................. 8907110 |

[51] Int. Cl.$^7$ .............................. C12N 15/00; C12N 1/19
[52] U.S. Cl. ................ 435/254.21; 435/254.11; 435/254.2; 435/69.1; 435/69.6; 536/23.1; 536/23.2; 536/23.74; 530/324
[58] Field of Search .................................. 435/91, 320.1, 435/254, 255, 256, 69.1, 69.6, 71.1, 172.3, 942, 471, 254.11, 254.21, 254.2; 536/27, 23.1, 23.2, 23.74; 935/9, 10, 28, 48, 56, 60, 68; 530/324

[56] References Cited

U.S. PATENT DOCUMENTS

| 4,546,082 | 10/1985 | Kurjan et al. | ................................ 435/6 |
| 4,929,553 | 5/1990 | Bussey et al. | ............................ 435/69.1 |
| 5,087,613 | 2/1992 | Courtney et al. | .......................... 514/12 |
| 5,162,208 | 11/1992 | Lemoine et al. | ........................ 435/69.1 |

FOREIGN PATENT DOCUMENTS

| 213593 | 3/1987 | European Pat. Off. . |
| 225633 | 6/1987 | European Pat. Off. . |
| 340170 | 11/1989 | European Pat. Off. . |
| 854418 | 2/1986 | South Africa . |

OTHER PUBLICATIONS

Strathern et al (eds.) 1981. in: The Molecular Biology of the Yeast Saccharomyces. Life Cycle and Inheritance. Cold Spring Harbor Laboratory. Cold Spring Harbor, New York. p458.
Mullenbach et al. 1986 J. Biol. Chem. 261, 719–722.
*Dictionary of Microbiology and Molecular Biology*, Second Edition (Singleton et al.) 1987. John Wiley & Sons., Chichester, p. 610.
Stryer, L. 1975. in: *Biochemistry*. W.H. Freeman and Company. San Francisco. p. 21.
Dodt et al., 1988. FEBS Lett. 229, 87–90.
Achstetter et al. Yeast, vol. 1, p. 139–157 (1985).
Achstetter et al. Embo. J., vol. 4, p 173–177 (1985).
Dmochowska et al., *Cell*, vol. 50, p. 573–584 (1987).
Wagner et al. Febs Letters, vol. 221, p 423–426 (1987).
Rendueles et al, Fems Microbiology Review, vol. 54, p 17–46 (1988).
George–Nascimento et al, Biochemistry, vol. 27, p. 797–802 (1988).
Vlasuk et al, J. Biological Chemistry, vol. 261, p. 4789–4796 (1986).
Kingsman et al., Biotechnol. Genet. Eng. Rev., vol. 3, p. 377–416(1985).

*Primary Examiner*—Christopher S. F. Low
*Attorney, Agent, or Firm*—Michael U. Lee; Myra H. McCormack

[57] ABSTRACT

A novel process for the production of heterologous proteins including the use of certain transformed protease deficient yeast strains is provided. The invention concerns also said transformed yeast strains and methods for the production thereof.

11 Claims, 16 Drawing Sheets

Fig. 2: In vitro synthesis of the PH05 signal sequence - hirudin HV1 gene with preferred yeast codons

```
        EcoRI                                    PH05 SS
       ---------1---------            3          --------
5'   AATTCAAAATGTTTAAATCTGTTGTTTATTCAATTTTAGCCGCTTCTTT
3'       GTTTTACAAATTTAGACAACAAATAAGTTAAAATCGGCGAAGAAA
            -----------2----------------         4

──→YHIR
       --5--------            7               -------------
       GGCCAATGCAGTTGTTTACACCGACTGTACCGAATCTGGTCAAAACTTGT
       CCGGTTACGTCAACAAATGTGGCTGACATGGCTTAGACCAGTTTTGAACA
         ----------6---------          8

-9----------              11             --------------13-
       GTTTGTGTGAAGGTTCTAACGTTTGTGGTCAAGTAACAAGTGTATCTTG
       CAAACACACTTCCAAGATTGCAAACACCAGTTCCATTGTTCACATAGAAC
            -----------10------------          12

---------               15              ---------------17
       GGTTCTGACGGTGAAAAGAACCAATGTGTTACCGGTGAAGGTACCCCAAA
       CCAAGACTGCCACTTTTCTTGGTTACACAATGGCCACTTCCATGGGGTTT
         ----------14--------           16         -----

-------------           19              ------------
       GCCACAATCTCACAACGACGGTGACTTCGAAGAAATCCCAGAAGAATACT
       CGGTGTTAGAGTGTTGCTGCCACTGAAGCTTCTTTAGGGTCTTCTTATGA
         -----18--------------------              20

-21-----
       TGCAATAG       3'
       ACGTTATCCTAG   5'
```

BamHI

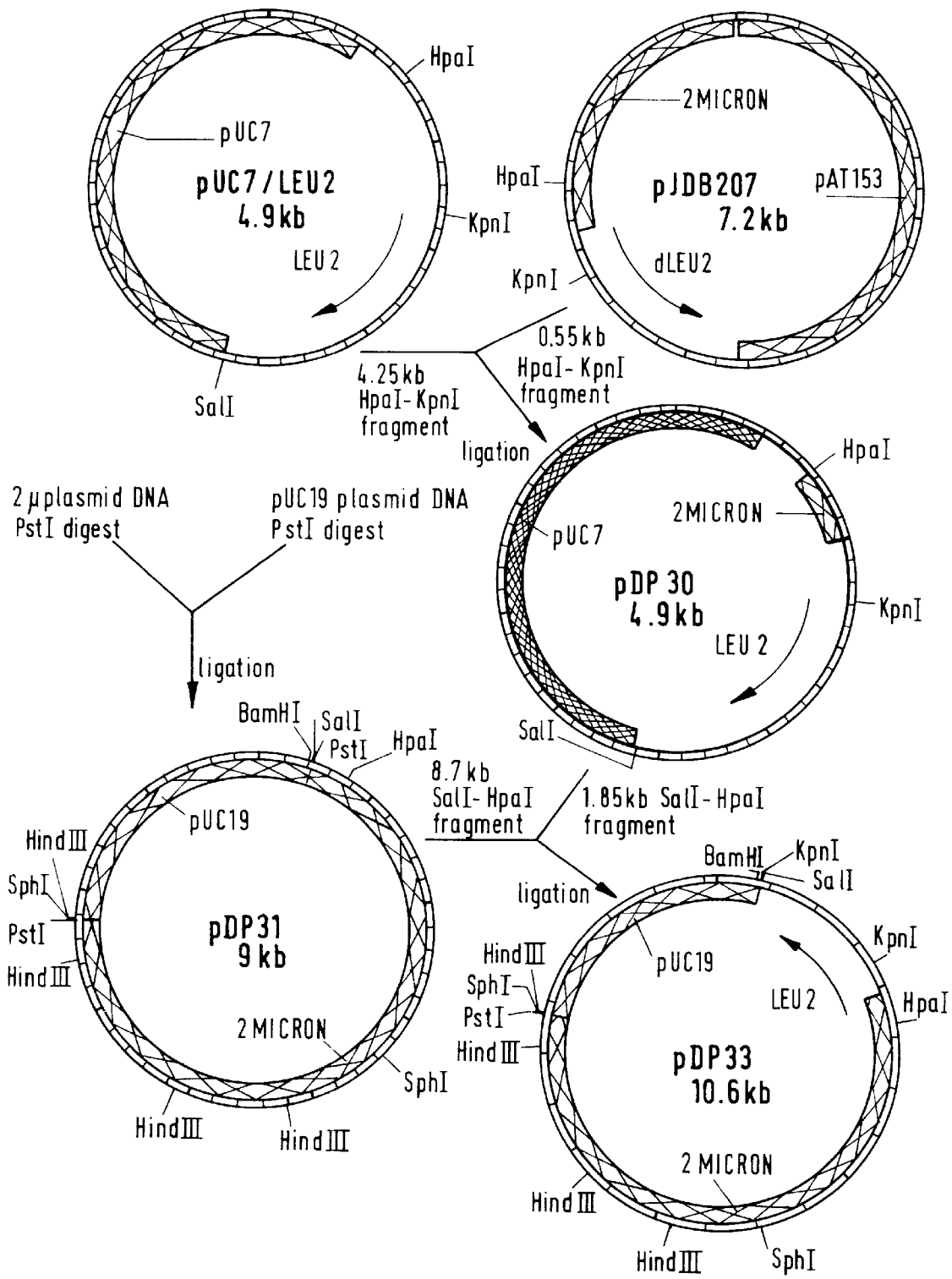
Fig. 3: CONSTRUCTION OF PLASMID pDP33

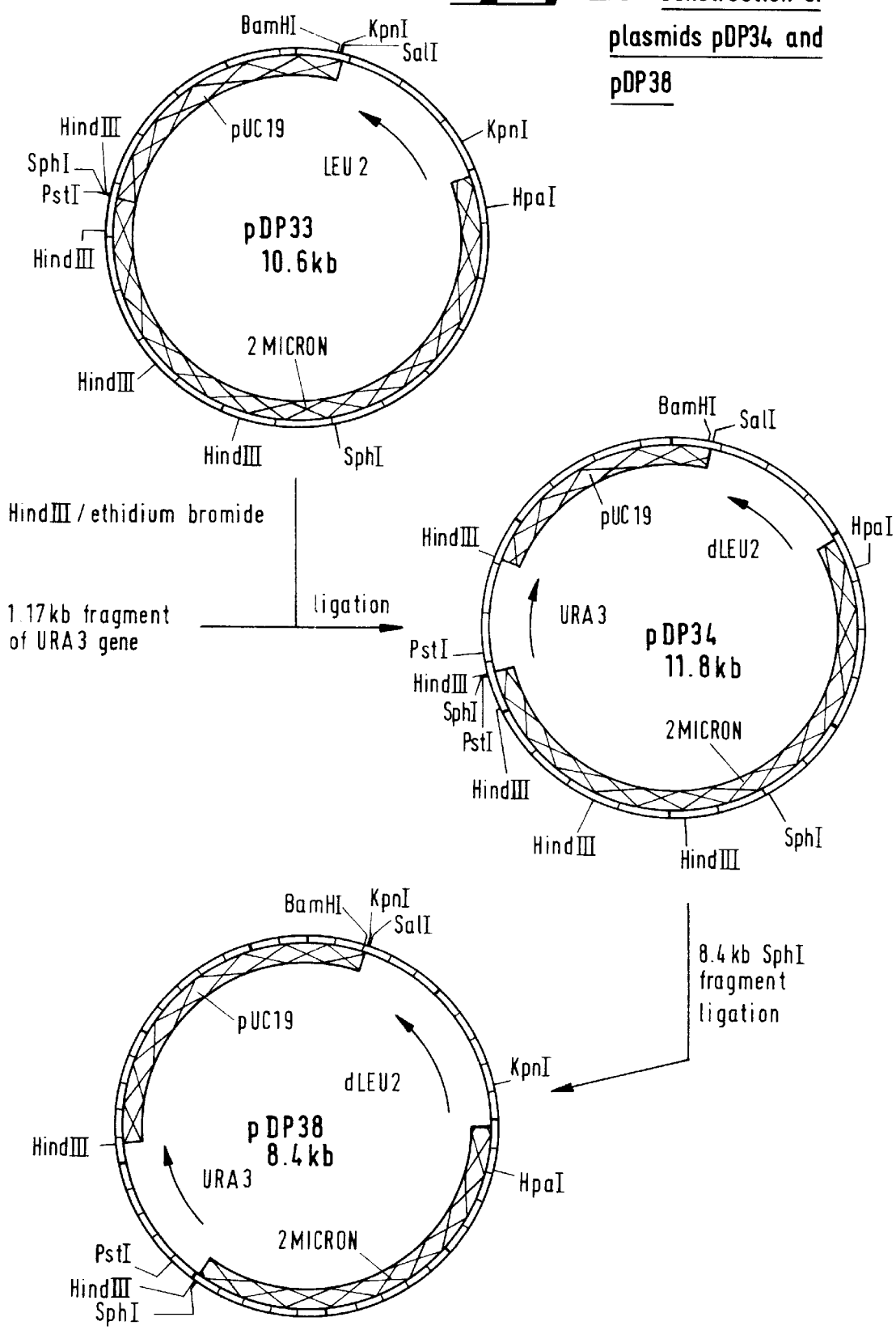
Fig. 4: Construction of plasmids pDP34 and pDP38

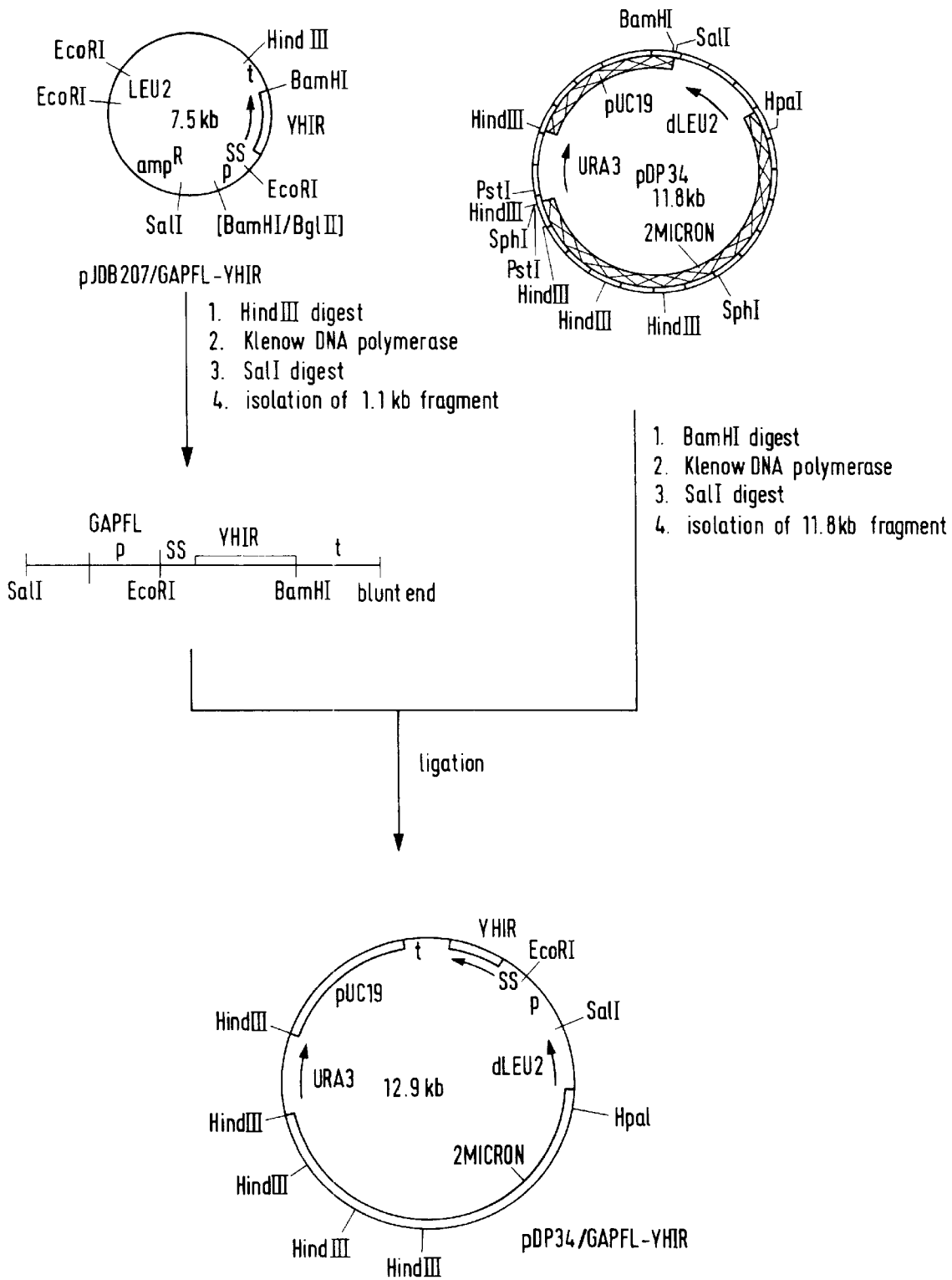
Fig. 5: Construction of plasmid pDP34/GAPFL-YHIR

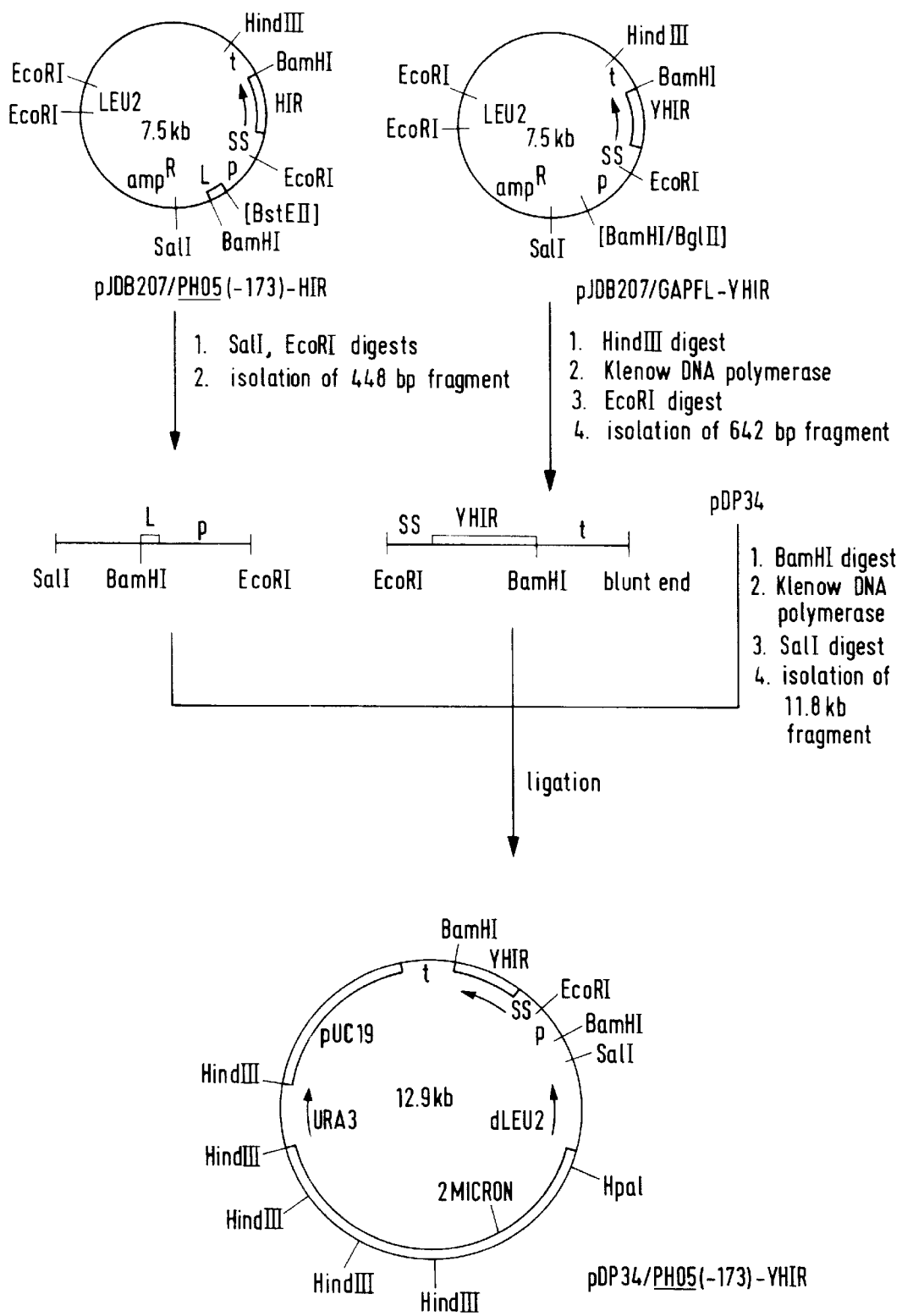
Fig. 6: Construction of plasmid pDP34/PHO5(-173)-YHIR

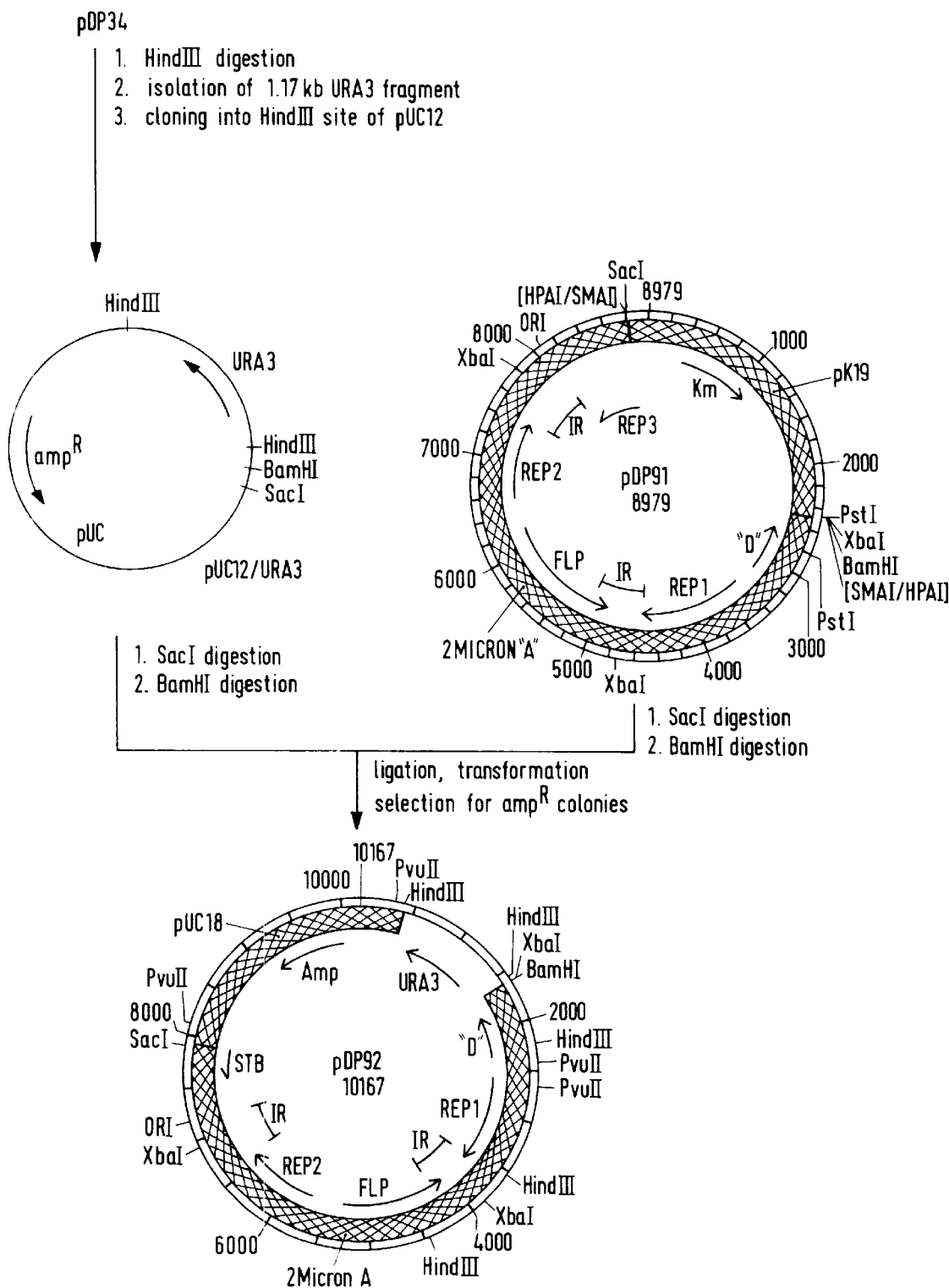
Fig. 7: Construction of plasmid pDP92

HIRUDIN MUTANT HV1-WQLR

FIG. 8E

HIRUDIN MUTANT HV1-WQLR

FIG. 8F

HIRUDIN MUTANT HV1-SFRY

BYSkex1

15.74
17.18

A₂₁₆

Time (min)

FIG. 8G

HIRUDIN MUTANT HV1-SFRY

BYSKEX1

Peaks: 15.66, 16.72, 17.17

FIG. 8H

PRODUCTION OF POLYPEPTIDES BY USE OF NOVEL PROTEASE DEFICIENT YEAST STRAINS

This application is a continuation of application Ser. No. 346,670, filed May 3, 1989 now abandoned.

The invention pertains to the field of recombinant DNA technology and concerns an improved method for the preparation of polypeptides with the aid of genetically engineered yeast cells, said genetically engineered yeast cells, and methods for the preparation of said yeast cells.

Recently, quite a number of heterologous proteins have been expressed in yeast after transformation of yeast cells with suitable expression vectors comprising DNA sequences coding for said proteins, like e.g. α-interferon [IFNα, Hitzeman et al. (1981) Nature 294, 717–722], lysozyme [Oberto et al. (1985) Gene 40, 57–65], α-amylase [Sato et al. (1986) Gene 50, 247–257], tissue-type plasminogen activator [t-PA, European Patent Application No. 143 081] or desulphatohirudin [European Patent Application No. 225 633]. In many cases, however, the heterologous proteins are not synthesized in pure form, but as a mixture containing partially degraded such as C-terminally shortened proteins. For instance, the expression of human atrial natriuretic peptide (hANP) in yeast resulted in the secretion of two forms of mature hANP differing in their C-terminus [Vlasuk et al. (1986) J. Biol. Chem. 261, 4798–4796]. The major form was lacking the last two amino acids of the protein (Arg 150 and Tyr 151) while the minor form was the full-length material. Similar results have been obtained after the expression of epidermal growth factor (EGF) in yeast [George-Nascimento et al. (1988) Biochemistry 27, 797–802] where the secreted expression products were heterogeneous in that sense that either the last (Arg 53) or the last two amino acids (Leu 52 and Arg 53) were missing and no full-length EGF was produced.

A polypeptide that quite recently has gained considerable attention to molecular biologists is hirudin, an anticoagulant agent occuring naturally in leeches (*Hirudo medicinalis*). Hirudin is not a single polypeptide species but a class of equally acting polypeptides consisting of at least four representatives designated hirudin variant 1 (HV1), hirudin variant 2 (HV2) [cf. European Patent Application No. 158 564], hirudin variant PA [cf. PCT-Application No. 86/03493] and "des-(Val)$_2$-hirudin" [cf. European Patent Application No. 158 986]. The variants differ in structure from each other by a number of amino acids (especially, the N-terminal sequence of HV1 is Val-Val-Tyr, that of HV2 and of PA is Ile-Thr-Tyr and that of "des-(Val)$_2$-hirudin" is Thr-Tyr) but have an accumulation of hydrophobic amino acids at the N-terminus and of polar amino acids at the C-terminus, a tyrosine residue (Tyr$^{63}$) present as sulphate monoester, three disulphide bridges and the anticoagulant activity in common.

Recently, cDNAs and synthetic genes coding for hirudin variants have been cloned and expressed in microbial hosts. Although the expression products lack the sulphate monoester group at Tyr$^{63}$— and were therefore designated "desulphatohirudins"—they turned out to exhibit approximately the same biological activity as the natural sulphated hirudins. Desulphatohirudin variant HV1 has been expressed in *Escherichia coli* [European Patent Applications No. 158 564 and 168 342] and in *Saccharomyces cerevisiae* [European Patent Applications No. 168 342, 200 655, 225 633 and 252 854]. Similarly, desulphatohirudin HV2 has been expressed in *Escherichia coli* [European Patent Applications No. 158 564] and in *Saccharomyces cerevisiae* [European Patent Application No. 200 655, PCT-Application No. 86/01224] and des-(Val)$_2$-desulphatohirudin has been expressed in *Escherichia coli* [European Patent Application No. 158 986].

Generally, expression efficiency and yields in hirudin compounds are higher when *S. cerevisiae* is chosen as the host microorganism. However, irrespective of the specific yeast host strain used the expression product turned out to be a heterogeneous mixture of desulphatohirudin species differing from each other in the C-terminal sequence. For example, the culture broths obtained from cultured yeast strains comprising the hirudin variant HV1 gene were found to contain desulphatohirudin HV1 contaminated with considerable amounts of analogs lacking the C-terminal amino acid Gln$^{65}$ or the C-terminal amino acids Leu$^{64}$ and Gln$^{65}$.

The separation of mixtures containing full-length proteins such as desulphatohirudin, hANP or EGF as well as C-terminally shortened derivatives thereof into the individual components and the purification of these components to homogeneity is laborious and time-consuming. Considering the incidental expenses there is a need for improved methods which render possible the economic production of homogeneous proteins such as desulphatohirudin in yeast. It is an object of the present invention to provide methods for the production of homogeneous heterologous proteins in yeast.

While it is evident that the isolation of C-terminally shortened derivatives of heterologous proteins from culture broths of transformed yeast strains containing the corresponding DNA sequence coding for said proteins is due to the post-translational action of endogenous yeast proteases on the primary expression product, e.g. integral desulphatohirudin, the specific protease(s) which is (are) responsible for the C-terminal degradation has (have) not been identified till now. The most important yeast proteases involved in protein degradation in general are endopeptidases yscA and yscB and carboxy exopeptidases yscY and yscS. The use of yeast strains which are defective in protease A, B, Y and/or S activity can partially reduce random proteolysis of foreign gene products such as desulphatohirudin. However, considerable amounts of proteins lacking one or two amino acids at the C-terminus are still observed.

Surprisingly, it has now been found that yeast mutant strains lacking carboxypeptidase yscα activity are unable to remove amino acids from the C-terminus of heterologous proteins and therefore give rise to integral (authentic) proteins. Carboxypeptidase yscα is a membrane-associated exopeptidase and plays, as is well known, an important role in the maturation of killer factor and mating factor α [cf. J. C. Wagner and D. H. Wolf (1987) FEBS Letters 221, 423]. It is the expression product of the KEX1 gene. According to the published data [cf. P. S. Rendueles and D. H. Wolf (1988) FEMS Microbiol. Rev. 54, 17], the action of yscα is strongly confined to C-terminal basic amino acid residues (Arg, Lys). In view of these data and the fact that the C-terminal amino acids of desulphatohirudin are not basic (for example, Gln and Leu in desulphatohirudin variant HV1), it is highly surprising and an unexpected result that the use of yeast mutant strains lacking carboxypeptidase yscα activity renders possible the production of homogeneous desulphatohirudin without any tedious separation of C-terminally shortened desulphatohirudin analogs being required.

The same holds true for other heterologous proteins like for example hANP, EGF or the connective tissue activating peptide-III [CTAP-III, Mullenbach et al. (1986) J. Biol. Chem. 261, 719–722] which can be produced in their full-length forms when a yeast mutant strain lacking carboxypeptidase yscα activity is used for transformation with an appropriate vector.

Accordingly, the invention relates to an improved method for the production of a protein heterologous to yeast in a homogeneous form comprising culturing a yeast strain which lacks carboxypeptidase yscα activity and has been transformed with a hybrid vector comprising a yeast promoter operably linked to a DNA sequence coding for said heterologous protein and isolating said heterologous protein.

In particular, the invention relates to an improved method for the production of a protein heterologous to yeast in a homogeneous form comprising culturing said yeast strain which has been transformed with a hybrid vector comprising a yeast promoter operably linked to a first DNA sequence encoding a signal peptide linked in the proper reading frame to a second DNA sequence coding for said heterologous protein and a DNA sequence containing yeast transcription termination signals, and isolating said heterologous protein.

Heterologous proteins which can be produced by the improved method according to the invention are such proteins which are susceptible to posttranslational C-terminal degradation by carboxypeptidase yscα after expression in yeast. Such heterologous proteins are characterized by two C-terminal amino acids selected from the group consisting of Lys, Arg, Tyr, Ala, Leu, Gln, Glu, Asp, Asn and Ser. The preferred heterologous proteins are those proteins which are mentioned above, especially desulphatohirudin.

In the most preferred aspect the invention relates to an improved method for the production of desulphatohirudin. comprising culturing a yeast strain which lacks carboxypeptidase yscα activity and has been transformed with a hybrid vector comprising a desulphatohirudin expression cassette consisting of a yeast promoter operably linked to a first DNA sequence encoding a signal peptide linked in the proper reading frame to a second DNA sequence coding for desulphatohirudin, and a DNA sequence containing yeast transcription termination signals, and isolating desulphatohirudin.

The term "desulphatohirudin" is intended to embrace the desulphatohirudin compounds described in literature or obtainable from a transformed microorganism strain containing DNA which codes for a desulphatohirudin. Such desulphatohirudins are, for example, desulphatohirudin variant HV1, HV1 (modified a, b), HV2, HV2 (modified a, b c), PA, variants of PA and des(Val₂)-desulphatohirudin.

Preferred desulphatohirudins are those having the formula

X$_1$ Tyr Thr Asp Cys Thr Glu Ser Gly Gln Asn Leu Cys Leu Cys Glu Gly Ser Asn Val Cys Gly Gln Gly Asn X$_2$ Cys Ile Leu Gly Ser Asp Gly Glu X$_3$ Asn Gln Cys Val Thr Gly Glu Gly Thr Pro X$_4$ Pro Gln Ser X$_5$ Asn Asp Gly Asp Phe Glu Glu Ile Pro Glu X$_6$

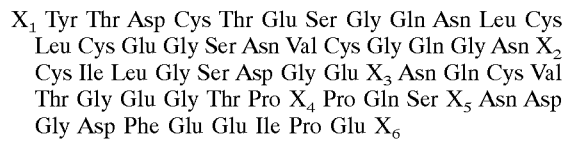

in which a) X$_1$ represents the dipeptide residue Val-Val and X$_2$, X$_3$ and X$_4$ are each Lys, X$_5$ is His and X$_6$ is the peptide residue Glu-Tyr-Leu-Gln (HV1), or b) X$_2$ is Ile or Glu and X$_1$ and X$_3$–X$_6$ are as defined in a) (HV1 modified a), or c) X$_3$ is Ile or Glu and X$_1$, X$_2$ and X$_4$–X$_6$ are as defined in a) (HV1 modified a), or d) X$_4$ is Ile or Glu and X$_1$–X$_3$ and X$_5$ and X$_6$ are as defined in a) (HV1 modified a), or e) X$_5$ is Leu or Asp and X$_1$–X$_4$ and X$_6$ are as defined in a) (HV1 modified a), or f) X$_6$ is selected from the group consisting of Glu-Tyr, Glu-Tyr-Leu, Glu-Asp-Leu-Gln, Glu-Glu-Leu-Gln, Glu-Tyr-Lys-Arg, Glu-Asp-Lys-Arg, Glu-Lys-Leu-Gln, Ser-Phe-Arg-Tyr, Trp-Glu-Leu-Arg, Glu-Tyr-Leu-Gln-Pro and Glu-Tyr-Leu-Gln-Arg and X$_1$–X$_5$ are as defined in a) (HV1 modified b), or g) in which X$_1$ represents Thr and X$_2$–X$_6$ are as defined in a) (des(Val$_2$)-desulphatohirudin), or having the formula Y$_1$ Tyr Thr Asp Cys Thr Glu Ser Gly Gln Asn Leu Cys Leu Cys Glu Gly Ser Asn Val Cys Gly Lys Gly Asn Lys Cys Ile Leu Gly Ser Asn Gly Lys Gly Asn Gln Cys Val Thr Gly Glu Gly Thr Pro Y$_2$ Pro Glu Ser His Asn Asn Gly Asp Phe Glu Glu Ile Pro Glu Glu Y$_3$ Leu Gln

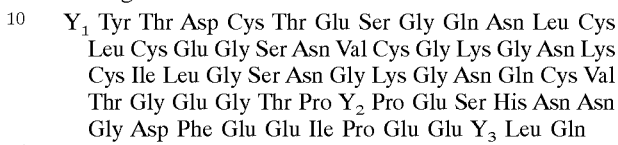

in which a) Y$_1$ represents the N-terminal dipeptide residue Ile-Thr, Y$_2$ is Asn and Y$_3$ is Tyr (HV2), or b) Y$_2$ is Lys, Arg or His and Y$_1$ and Y$_3$ are as defined in a) (HV2 modified a), or c) Y$_3$ is Glu or Asp and Y$_1$ and Y$_2$ are as defined in a) (HV2 modified b), or d) in which Y$_1$ represents the N-terminal dipeptide residue Val—Val and Y$_2$ and Y$_3$ are as defined in a) (HV2 modified c), or having the formula Ile Thr Tyr Thr Asp Cys Thr Glu Ser Gly Gln Asn Leu Cys Leu Cys Glu Gly Ser Asn Val Cys Gly Lys Gly Asn Lys Cys Ile Leu Gly Ser Gln Gly Lys Asp Asn Gln Cys Val Thr Gly Glu Gly Thr Pro Lys Pro Gln Ser His Asn Gln Gly Asp Phe Glu Pro Ile Pro Glu Asp Ala Tyr Asp Glu

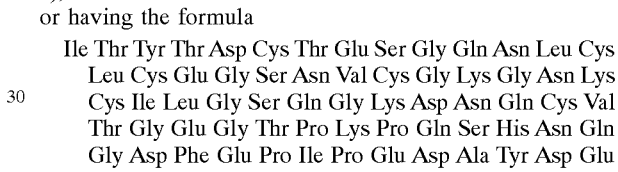

(PA) and variants of said PA which are characterized by a shortening of the primary structure by 1 or 2 amino acids at the N-terminus or by 18, 10, 9, 6, 4 or 2 amino acids at the C-terminus.

The most preferred desulphatohirudin compound is that of formula I in which X$_1$–X$_6$ are as defined in a).

The yeast host strains and the constituents of the hybrid vectors are those specified below.

The transformed yeast strains are cultured using methods known in the art.

Thus, the transformed yeast strains according to the invention are cultured in a liquid medium containing assimilable sources of carbon, nitrogen and inorganic salts.

Various carbon sources are usable. Example of preferred carbon sources are assimilable carbohydrates, such as glucose, maltose, mannitol, fructose or lactose, or an acetate such as sodium acetate, which can be used either alone or in suitable mixtures. Suitable nitrogen sources include, for example, amino acids, such as casamino acids, peptides and proteins and their degradation products, such as tryptone, peptone or meat extracts, furthermore yeast extract, malt extract, corn steep liquor, as well as ammonium salts, such as ammonium chloride, sulphate or nitrate which can be used either alone or in suitable mixtures. Inorganic salts which may be used include, for example, sulphates, chlorides, phosphates and carbonates of sodium, potassium, magnesium and calcium. Additionally, the nutrient medium may also contain growth promoting substances. Substances which promote growth include, for example, trace elements, such as iron, zinc, manganese and the like, or individual amino acids.

Due to the incompatibility between the endogenous two-micron DNA and hybrid vectors carrying its replicon, yeast cells transformed with such hybrid vectors tend to lose the latter. Such yeast cells have to be grown under selective conditions, i.e. conditions which require the expression of a plasmid-encoded gene for growth. Most selective markers currently in use and present in the hybrid vectors according to the invention (infra) are genes coding for enzymes of amino acid or purine biosynthesis. This makes it necessary to use synthetic minimal media deficient in the corresponding amino acid or purine base. However, genes conferring resistance to an appropriate biocide may be used as well [e.g. a gene conferring resistance to the amino-glycoside G418]. Yeast cells transformed with vectors containing antibiotic resistance genes are grown in complex media containing the corresponding antibiotic whereby faster growth rates and higher cell densities are reached.

Hybrid vectors comprising the complete two-micron DNA (including a functional origin of replication) are stably maintained within strains of Saccharomyces cerevisiae which are devoid of endogenous two-micron plasmids (so-called cir° strains) so that the cultivation can be carried out under non-selective growth conditions, i.e. in a complex medium.

Yeast cells containing hybrid plasmids with a constitutive promoter (e.g. ADHI, GAPDH) express the DNA encoding a heterologous protein controlled by said promoter without induction. However, if said DNA is under the control of a regulated promoter (e.g. PGK or PHO5) the composition of the growth medium has to be adapted in order to obtain maximum levels of mRNA transcripts, i.e. when using the PHO5 promoter the growth medium must contain a low concentration of inorganic phosphate for derepression of this promoter.

The cultivation is carried out by employing conventional techniques. The culturing conditions, such as temperature, pH of the medium and fermentation time are selected in such a way that maximal levels of the heterologous protein are produced. A chosen yeast strain is preferably grown under aerobic conditions in submerged culture with shaking or stirring at a temperature of about 25° to 35° C., preferably at about 28° C., at a pH value of from 4 to 7, for example at approximately pH 5, and for at least 1 to 3 days, preferably as long as satisfactory yields of protein are obtained.

The heterologous proteins expressed in yeast can be accumulated inside the cells or can be secreted into the culture medium. In the case of desulphatohirudin irrespective of the yeast strain, promoter and signal peptide used, most of the produced protein is secreted into the culture medium whereas only a minor part remains cell associated. The precise ratio (secreted compounds/cell associated compounds) depends on the fermentation conditions and the recovery process applied. In general it amounts to about or more than 8:1. Accordingly, secreted desulphatohirudin is always strongly dominating.

The heterologous protein can be isolated from the culture medium by conventional means. For example, the first step consists usually in separating the cells from the culture fluid by means of centrifugation. The resulting supernatant can be enriched for heterologous protein by treatment with polyethyleneimine so as to remove most of the non-proteinaceous material, and precipitation of the proteins by saturating the solution with ammonium sulphate. Host proteins, if present, can also be precipitated by means of acidification with acetic acid (for example 0.1%, pH 4–5). A further enrichment of the heterologous protein can be achieved by extracting the acetic acid supernatant with n-butanol. Other purification steps include, for example, desalination, chromatographic processes, such as ion exchange chromatography, gel filtration chromatography, partition chromatography, HPLC, reversed phase HPLC and the like. The separation of the constituents of the protein mixture is also effected by dialysis, according to charge by means of gel electrophoresis or carrier-free electrophoresis, according to molecular size by means of a suitable Sephadex column, by affinity chromatography, for example with antibodies, especially monoclonal antibodies, or with thrombin coupled to a suitable carrier for affinity chromatography, or by other processes, especially those known from the literature.

If the heterologous protein is not secreted or if it is desired to isolate any additional heterologous protein which is cell associated, i.e. which has accumulated intracellularly or in the periplasmic space, some supplementary purification steps are required. Thus, in case the heterologous protein has accumulated within the cells, the first step for the recovery thereof consists in liberating it from the cell interior. In most procedures the cell wall is first removed by enzymatic digestion with glucosidases (infra). Subsequently, the resulting spheroplasts are treated with detergents, such as Triton. Alternatively, mechanical forces, such as shearing forces (for example X-press, French-press) or shaking with glass beads, are suitable for breaking cells. In the case where the heterologous protein is secreted by the host cells into the periplasmic space, a simplified protocol can be used: The heterologous protein is recovered without cell lysis by enzymatic removal of the cell wall or by treatment with chemical agents, e.g. thiol reagents or EDTA, which give rise to cell wall damages permitting the product to be released.

In the case of desulphatohirudin the test with anti-hirudin or anti-desulphatohirudin antibodies (for example, monoclonal antibodies obtainable from hybridoma cells), the thrombin test [M. U. Bergmeyer (ed.), Methods in Enzymatic Analysis, Vol. II, p. 314–316, Verlag Chemie, Weinheim (FRG) 1983] or the blood coagulation test [F. Markwardt et al. (1982) Thromb. Haemost. 47, 226] can be used to detect the hirudin activity in fractions obtained in the course of the purification procedure. Analogous assays known from the literature can be used to detect other heterologous proteins.

The transformed yeast host cells according to the invention can be prepared by recombinant DNA techniques comprising the steps of preparing a hybrid vector comprising a yeast promoter operably linked to a DNA sequence coding for a heterologous protein, especially a hybrid vector comprising a yeast promoter operably linked to a first DNA sequence encoding a signal peptide linked in the proper reading frame to a second DNA sequence encoding a heterologous protein and a DNA sequence containing yeast transcription termination signals, if necessary, providing a mutant yeast strain which lacks carboxypeptidase yscα activity, transforming the mutant yeast strain obtained with said hybrid vector, and selecting transformed yeast cells from untransformed yeast cells.

Expression vectors

The yeast hybrid vectors according to the invention comprise a yeast promoter operably linked to a DNA sequence coding for a heterologous protein. Preferred hybrid vectors comprise a yeast promoter operably linked to a first DNA sequence encoding a signal peptide linked in the proper reading frame to a second DNA sequence encoding a heterologous protein such as desulphatohirudin and a DNA sequence containing yeast transcription termination signals.

The yeast promoter is a regulated promoter such as the PHO5, MFα1 or GAL1 promoter, or a constitutive promoter. In case of the expression of desulphatohirudin, a constitutive promoter is preferred. The constitutive yeast promoter is preferably derived from a highly expressed yeast gene, such as a gene encoding a glycolytic enzyme, such as the promoter of the enolase, glyceraldehyde-3-phosphate dehydrogenase (GAPDH), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase gene, furthermore the ADHI or TRPI promoter and a shortened acid phosphatase PHO5 promoter which has been deprived of its upstream activation sites. Especially preferred is the GAPDH promoter and functional fragments thereof starting at nucleotide between −550 and −180, in particular at nucleotide −540, −263 or −198, and ending at nucleotide −5 of the GAPDH gene, and shortened constitutive PHO5 promoters starting at nucleotide between −200 and −150, in particular at −173, and ending at nucleotide −9 of the PHO5 gene.

The DNA sequence encoding a signal peptide ("signal sequence") is preferably derived from a yeast gene coding for a polypeptide which is ordinarily secreted. The hirudin signal sequence obtainable from leech genome DNA or other signal sequences of heterologous proteins, which are ordinarily secreted can also be chosen. Yeast signal sequences are, for example, the signal and prepro sequences of the yeast invertase, α-factor, pheromone peptidase (KEX1), "killer toxin" and repressible acid phosphatase (PHO5) genes and the glucoamylase signal sequence from *Aspergillus awamori*. Alternatively, fused signal sequences may be constructed by ligating part of the signal sequence (if present) of the gene naturally linked to the promoter used (for example PHO5), with part of the signal sequence of hirudin or of another heterologous protein. Those combinations are favoured which allow a precise cleavage between the signal sequence and e.g. the desulphatohirudin amino acid sequence. Additional sequences, such as pro- or spacer-sequences which may or may not carry specific processing signals can also be included in the constructions to facilitate accurate processing of precursor molecules. Alternatively, fused proteins can be generated containing internal processing signals which allow proper maturation in vivo or in vitro. For example, the processing signals contain a Lys-Arg residue, which is recognized by a yeast endopeptidase located in the Golgi membranes. The preferred signal sequences according to the present invention are those of the yeast PHO5 gene coding for a signal peptide having the formula Met Phe Lys Ser Val Val Tyr Ser Ile Leu Ala Ala Ser Leu Ala Asn Ala, and of the yeast invertase gene coding for a signal peptide having the formula Met Leu Leu Gln Ala Phe Leu Phe Leu Leu Ala Gly Phe Ala Ala Lys Ile Ser Ala.

Genomic DNA sequences coding for a heterologous protein can be isolated from natural sources or a copy DNA (cDNA) can be produced from the corresponding complementary mRNA or by means of chemical and enzymatic processes, in a manner known per se.

For example, the DNA sequence coding for desulphatohirudin is known or can be isolated from genomic leech DNA or a complementary double-stranded desulphatohirudin DNA (desulphatohirudin ds cDNA) is produced from desulphatohirudin mRNA, or a gene coding for the amino acid sequence of desulphatohirudin is produced by means of chemical and enzymatic processes.

A DNA sequence containing yeast transcription termination signals is preferably the 3' flanking sequence of a yeast gene which contains proper signals for transcription termination and polyadenylation. Suitable 3' flanking sequences are for example those of the yeast gene naturally linked to the promoter used. The preferred flanking sequence is that of the yeast PHO5 gene.

The yeast promoter, the optional DNA sequence coding for the signal peptide, the DNA sequence coding for a heterologous protein and the DNA sequence containing yeast transcription termination signals are operably linked to each other, i.e. they are juxtaposed in such a manner that their normal functions are maintained. The array is such that the promoter effects proper expression of the heterologous gene (optionally preceded by a signal sequence), the transcription termination signals effect proper termination of transcription and polyadenylation and the optional signal sequence is linked in the proper reading frame to the heterologous gene in such a manner that the last codon of the signal sequence is directly linked to the first codon of the gene coding for the heterologous protein and secretion of the protein occurs. If the promoter and the signal sequence are derived from different genes, the promoter is preferably joined to the signal sequence between the major mRNA start and the ATG of the gene naturally linked to the promoter. The signal sequence should have its own ATG for translation initiation. The junction of these sequences may be effected by means of synthetic oligodeoxynucleotide linkers carrying the recognition sequence of an endonuclease.

Apart from the expression cassette, the hybrid vectors according to the invention comprise a yeast replication origin. Accordingly, the hybrid vectors comprise a DNA segment originating from two-micron DNA containing the origin of replication or, if a two-micron DNA free strains of yeast are used, total two-micron DNA. The latter type of vectors is preferred. The preferred hybrid vectors according to the invention contain the complete two-micron DNA in an uninterrupted form, i.e. two-micron DNA is cleaved once with a restriction endonuclease, the linearised DNA is linked with the other components of the vector prior to recircularization. The restriction site is chosen such that normal function of the REP1, REP2 and FLP genes and of the ORI, STB, IR1 and IR2 sites of two-micron DNA is maintained. Optionally, the restriction site is chosen such that the D gene of two-micron DNA too is kept intact. Preferred restriction sites are the unique PstI site located within the D gene and the unique HpaI and SnaBI sites located outside of all said genes and sites.

Preferably, the hybrid vectors according to the invention include one or more, especially one or two, selective genetic markers for yeast and such a marker and an origin of replication for a bacterial host, especially *Escherichia coli*.

As to the selective gene markers for yeast, any marker gene can be used which facilitates the selection for transformants due to the phenotypic expression of the marker gene. Suitable markers for yeast are, for example, those expressing antibiotic resistance or, in the case of auxotrophic yeast mutants, genes which complement host lesions. Corresponding genes confer, for example, resistance to the antibiotics G418, hygromycin or bleomycin or provide for prototrophy in an auxotrophic yeast mutant, for example the URA3, LEU2, LYS2 or TRP1 gene.

As the amplification of the hybrid vectors is conveniently done in *E. coli*, an *E. coli* genetic marker and an *E. coli* replication origin are included advantageously. These can be obtained from *E. coli* plasmids, such as pBR322 or a pUC plasmid, for example pUC18 or pUC19, which contain both *E. coli* replication origin and *E. coli* genetic marker conferring resistance to antibiotics, such as ampicillin.

The hybrid vectors according to the invention are prepared by methods known in the art, for example by linking the expression cassette comprising a yeast promoter operably linked to a DNA sequence coding for a heterologous protein, and the DNA fragments containing selective genetic markers for yeast and for a bacterial host and origins of replication for yeast and for a bacterial host in the predetermined order.

Yeast Strains Lacking Carboxypeptidase yscα Activity

The yeast strains according to the invention lack carboxypeptidase yscα activity. Preferably, the yeast strains are double, triple or quadruple mutants, i.e. are defective in further yeast peptidases activity.

A wide variety of proteinases, like those mentioned, have been characterized in the yeast *Saccharomyces cerevisiae* [see T. Achstetter and D. H. Wolf (1985) Yeast 1, 139–157]. Mutants lacking activity of most of these proteases have been isolated and studied biochemically. The consequences of the absence of certain proteases were elucidated and some properties proved to be useful for the de novo isolation of protease-deficient mutants. Since spontaneous mutation frequencies are low, yeast is usually treated with mutagens such as X-ray or U.V. radiation or chemical mutagens which are remarkably efficient and can induce mutations at a rate of $1 \cdot 10^{-4}$ to $10^{-3}$ per gene without a great deal of killing. The proteases which are lacking in the yeast strains according to the invention do not perform indispensible functions in the cell metabolism; therefore mutations which completely destroy the activity of these proteins are not lethal. Each mutant type of the proteases mentioned (yscα, yscB, yscA, yscY and yscS) can be isolated separately after mutagenesis. Isolation and selection is based on colony screening assays which are well-known in the art.

A second and more efficient method to introduce the desired single or multiple protease deficiencies into the yeast genome is the site-directed mutagenesis or gene-disruption or gene replacement [cf. H. Rudolph et al., Gene, 36 (1985) 87–95]. When the genetic sequence is known, as it is, for example, the case in protease yscb, carboxypeptidase yscY and carboxypeptidase yscα, the genomic protease gene can be made defective by insertion, substitution or deletion making use of the well-known site-directed mutagenesis procedure [see, for example, M. J. Zoller and M. Smith (1983) Methods Enzymol. 100, 468] which involves the preparation of an appropriately devised mutagenic oligodeoxyribonucleotide primer. Alternatively, the genomic protease gene can be replaced by foreign DNA or said foreign DNA can be inserted into a suitable restriction site of the protease gene. For example, in order to prepare a yeast mutant lacking peptidase yscα activity (kex⁻ mutant) foreign DNA is inserted into a suitable restriction site occurring in the genomic KEX1 gene. In case the yeast strain used has a defect in a chromosomal gene coding for an enzyme of amino acid or purine biosynthesis a corresponding intact gene can be inserted into the chromosomal KEX1 gene thus providing for prototrophy in the auxotrophic yeast strain and changing the genotype at the same time from KEX1 to kex1. The gene replacement or directed mutagenesis procedures are commonly applied in the art and are absolutely reproducible.

The current method to compose multiple protease-defective strains, such as strains lacking yscα and yscB activity, consists in meiotic crossing and subsequent tetrad analysis. The tetrads, which derive from the diploid cells, are dissected according to standard genetic techniques. Random assortment among the four spores of a tetrad allows the construction of double and multiple mutants in subsequent crosses. Random spore analysis can also be used as an alternative system.

Since mutants devoid of individual proteases and even double mutants are available from yeast genetic stock centers, triple and quadruple mutants can reproducibly be combined by known successive meiotic crossing techniques.

Suitable starting strains of *Saccharomyces cerevisiae* include, for example, the kex1 strain 96 obtainable from the Yeast Genetic Stock Center, Berkeley, yeast peptidases A (yscA) negative strains AB103 (ATCC20673) and AB110 (ATCC20796), yeast peptidase B (yscB) negative strains HT246, H426 and H449 (the latter is, in addition, cir°) deposited at the Deutsche Sammlung von Mikroorganismen, Braunschweig, FRG, under accession numbers 4084, 4231 and 4413, respectively, yeast peptidases B, Y and S (yscB, yscY and yscS) negative strain BYS232-31-42 and yeast peptidases A, B, Y and S (yscA, yscB, yscy and yscS) negative strain ABYS.

As mentioned above, the preferred yeast strains according to the invention are devoid of endogenous two-micron DNA. The two-micron plasmid is a high copy number, self-replicating, extrachromosomal DNA element, contained in most strains of *Saccharomyces cerevisiae*. The most striking structural features of the two-micron plasmid are two inverted repeats (IR1 and IR2) of 559 bp each dividing the plasmid in two DNA regions of different length. The homologous recombination between these two identical IR sequences results in the formation of two molecular isomers (form A and form B). Stability of the two-micron plasmid is given by three plasmid encoded functions. The REP1 and REP2 gene products are trans-acting proteins that are required for the stable partitioning of the two-micron plasmid. Of these two, REP1 is possibly the more important, in that the efficiency of partitioning is dependent on the gene dosage of the REP1 gene product [A. Cashmore et al. (1986) Mol. Gen. Genet. 203, 154]. These two proteins act through and on the STB (REP3) site, an important cis-acting element on the plasmid [M. Jayaram et al. (1985) Mol. Cell. Biol. 5, 2466–2475; B. Viet et al. (1985) Mol. Cell. Biol. 5, 2190–2196].

Such cir° strains of *Saccharomyces cerevisiae* are known or can be prepared by methods known in the art [see, for example, C. P. Hollenberg (1982) Curr. Top. Microbiol. Immun. 96, 119]. The following alternative procedure for the preparation of cir° strains is based on the presumption that curing of the two-micron plasmid by a second plasmid involves increasing the dosage of the STB site to titrate out the REP1 and REP2 proteins. This relative reduction of the REP1 and REP2 proteins would lead to an instability of the endogenous two-micron plasmid.

Preferably, the second plasmid used has a defect in or lacks the REP1 gene. An example of such a plasmid is pDP38 which apart from the REP1 gene lacks an inverted repeat (IR2). This makes its high copy number expression dependent on the complementation of REP1 protein by the endogenous two-micron plasmid. It contains two yeast selective markers: URA3, used in both high and low copy number situations, and dLEU2, applicable only in high copy number situations [E. Erhart et al. (1968) J. Bacteriol. 625].

A yeast strain which is Ura⁻ and Leu⁻ is transformed with plasmid pDP38 and selected for Ura⁺ colonies. The selection on uracile free plates (Ura selection) gives a much better transformation frequency than the selection on leucine free plates (Leu selection), as the URA3 gene is much better expressed than the defective dLEU2 gene. A single colony is selected and streaked onto a Leu selection plate which gives colonies of varying sizes and form. Some of the smallest colonies are restreaked onto Ura selection plates and replica-plated onto Leu selection plates. Those colonies are selected that can grow under Ura selection but only very slowly under Leu selection. Growth on Ura selection plates shows that the plasmid pDP38 is still present and that the merely slow growth under Leu selection is not due to the loss of this plasmid, and the failure of growth under Leu selection implies that pDP38 is not able to complement this marker. The latter fact can be explained in two ways: A. The LEU2 gene on pDP38 is mutated, or B: The plasmid cannot complement leu2 because it cannot raise its copy number, implying that the two-micron plasmid is not available (i.e. lost) to complement the REP1 gene product.

These two possibilities can be distinguished very easily. In the first place, the minimal growth seen with said colonies (as against the absolute zero growth of cells without pDP38) shows that some LEU2 expression is present. The second point can be directly tested, as in the absence of the two-micron plasmid pDP38 will act only as an ARS type plasmid, i.e. it will be very unstable so that most of the colonies will lose it after a few generations. Accordingly, when a single colony is streaked onto a YPD plate, and single colonies taken and replica-plated onto uracile free plates, then only a few will grow under Ura selection. Non growing colonies are checked by hybridization for pUC and two-micron sequences. Colonies which show no hybridization signals are free of plasmid pDP38 and of endogenous two-micron plasmids (cir° strains). The cir° strains obtained can be treated as described above to yield yeast mutant strains which lack peptidase, especially yscα, activity and, in addition, are devoid of two-micron DNA.

In addition to the lack of yscα activity the preferred yeast strains according to the invention also lack further peptidases selected from the group consisting of yscA, yscB, yscY and yscS and are devoid of two-micron DNA. The most preferred yeast strains lack yscα and yscY activity and can optionally also be devoid of yscB and yscS or of yscA and yscB activity, and are devoid of two-micron DNA.

The yeast strains according to the invention can advantageously be used for the production of heterologous proteins. Surprisingly it was found that kex1 strains according to the invention carrying a hybrid vector containing a gene coding for a protein heterologous to yeast produce said protein in a homogenous form, i.e. lacking any C-terminally shortened byproducts.

Transformed Yeast Strains

The invention concerns furthermore a yeast strain which lacks carboxypeptidase yscα activity and has been transformed with a hybrid vector comprising a yeast promoter operably linked to a DNA sequence coding for a heterologous protein, and to a method for the production thereof.

Suitable yeast host strains include strains of *Saccharomyces cerevisiae* lacking carboxypeptidase yscα activity and optionally additional peptidase activity and which, optionally, have been cured of endogenous two-micron plasmids (see above).

The method for the production of said transformed yeast strain comprises transforming a yeast strain which lacks carboxypeptidase yscα activity with said hybrid vector.

The transformation of yeast with the hybrid vectors according to the invention may be accomplished according to the method described by Hinnen et al. [Proc. Natl. Acad. Sci. USA 75, 1929 (1978)]. This method can be divided into three steps:

(1) Removal of the yeast cell wall or parts thereof using various preparations of glucosidases, such as snail gut juices (e.g. Glusulase® or Helicase®) or enzym mixtures obtained from microorganisms (e.g. Zymolyase®) in osmotically stabilized solutions (e.g. 1 M sorbitol).

(2) Treatment of "naked" yeast cells (spheroplasts) with the DNA vector in the presence of PEG (polyethyleneglycol) and $Ca^{2+}$ ions.

(3) Regeneration of the cell wall and selection of the transformed cells in a solid layer of agar. This regeneration is conveniently done by embedding the spheroplasts into agar. For example, molten agar (about 50° C.) is mixed with the spheroplasts. Upon cooling the solution to yeast growth temperatures (about 30° C.), a solid layer is obtained. This agar layer is to prevent rapid diffusion and loss of essential macromolecules from the spheroplast and thereby facilitates regeneration of the cell wall. However, cell wall regeneration may also be obtained (although at lower efficiency) by plating the spheroplasts onto the surface of preformed agar layers.

Preferably, the regeneration agar is prepared in a way to allow regeneration and selection of transformed cells at the same time. Since yeast genes coding for enzymes of amino acid or nucleotide biosynthetic pathways are generally used as selective markers (supra), the generation is preferably performed in yeast minimal medium agar. If very high efficiencies of regeneration are required the following two step procedure is advantageous: (1) regeneration of the cell wall in a rich complex medium, and (2) selection of the transformed cells by replica plating the cell layer onto selective agar plates.

Another embodiment of the invention is a desulphatohirudin of the formula $X_1$ Tyr Thr Asp Cys Thr Glu Ser Gly Gln Asn Leu Cys Leu Cys Glu Gly Ser Asn Val Cys Gly Gln Gly Asn $X_3$ Cys Ile Leu Gly Ser Asp Gly Glu $X_2$ Asn Gln Cys Val Thr Gly Glu Gly Thr Pro $X_4$ Pro Gln Ser $X_5$ Asn Asp Gly Asp Phe Glu Glu Ile Pro Glu $X_6$ (IV), in which $X_1$ represents the dipeptide residue Val-Val, $X_2$, $X_3$ and $X_4$ are Lys, $X_5$ is His and $X_6$ is selected from the group consisting of Glu-Tyr-Lys-Arg, Ser-Phe-Arg-Tyr and Trp-Glu-Leu-Arg.

The known heterologous proteins obtainable by the process according to the invention can be used in a manner known per se, e.g. in the therapy and prophylaxis of human and animal diseases. For instance, human ANP exhibits natriuretic, diuretic and vasorelaxant activities and can be used in the regulation of cardiovascular homeostasis.

The desulphatohirudin compounds can be used, analogously to natural hirudin, for the therapy and prophylaxis of thrombosis, for acute shock therapy, for the therapy of consumption coagulopathies, and the like as described in European Patent Application No. 168 342.

The invention concerns especially the transformed yeast strains, the methods for the production thereof and the method for the production of heterologous proteins, as described in the Examples.

BRIEF DESCRIPTION OF THE DRAWINGS

In the following experimental part various embodiments of the present invention are described with reference to the accompanying drawings in which:

FIG. 2 is a schematic diagram showing the in vitro synthesis of the hirudin HV1 gene including the PHO5 signal sequence with the preferred yeast codons. The 21 oligodeoxynucleotides used are indicated by numbered lines and dotted lines, respectively.

FIG. 3 schematically illustrates the construction of plasmid pDP33.

FIG. 4 schematically illustrates the construction of plasmids pDP34 and pDP38.

FIG. 5 schematically illustrates the construction of expression plasmid pDP34/GAPFL-YHIR.

FIG. 6 schematically illustrates the construction of expression plasmid pDP34/PHO5(–173)-YHIR.

FIG. 7 schematically illustrates the construction of plasmid pDP92.

Figure 8E:
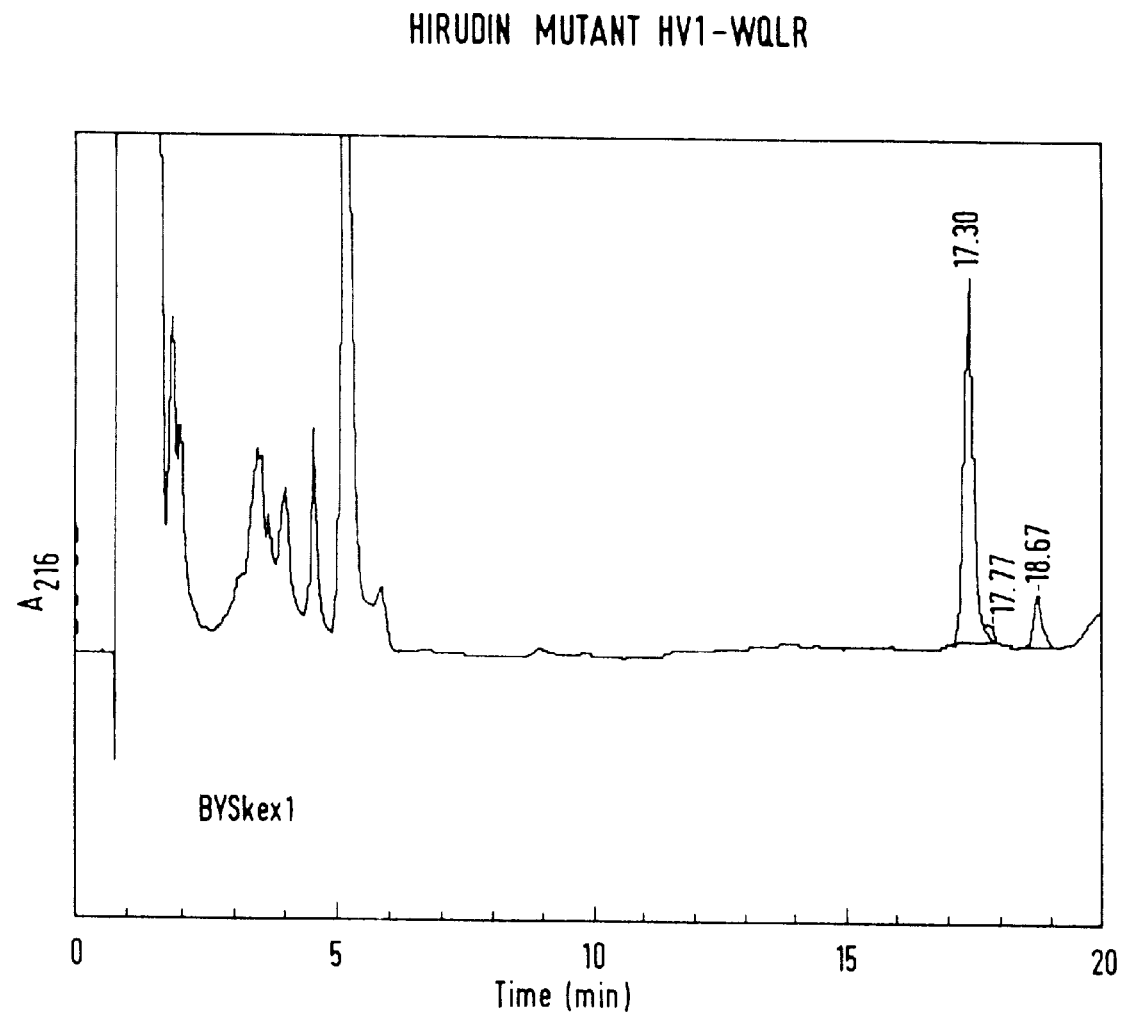
Figure 8F:
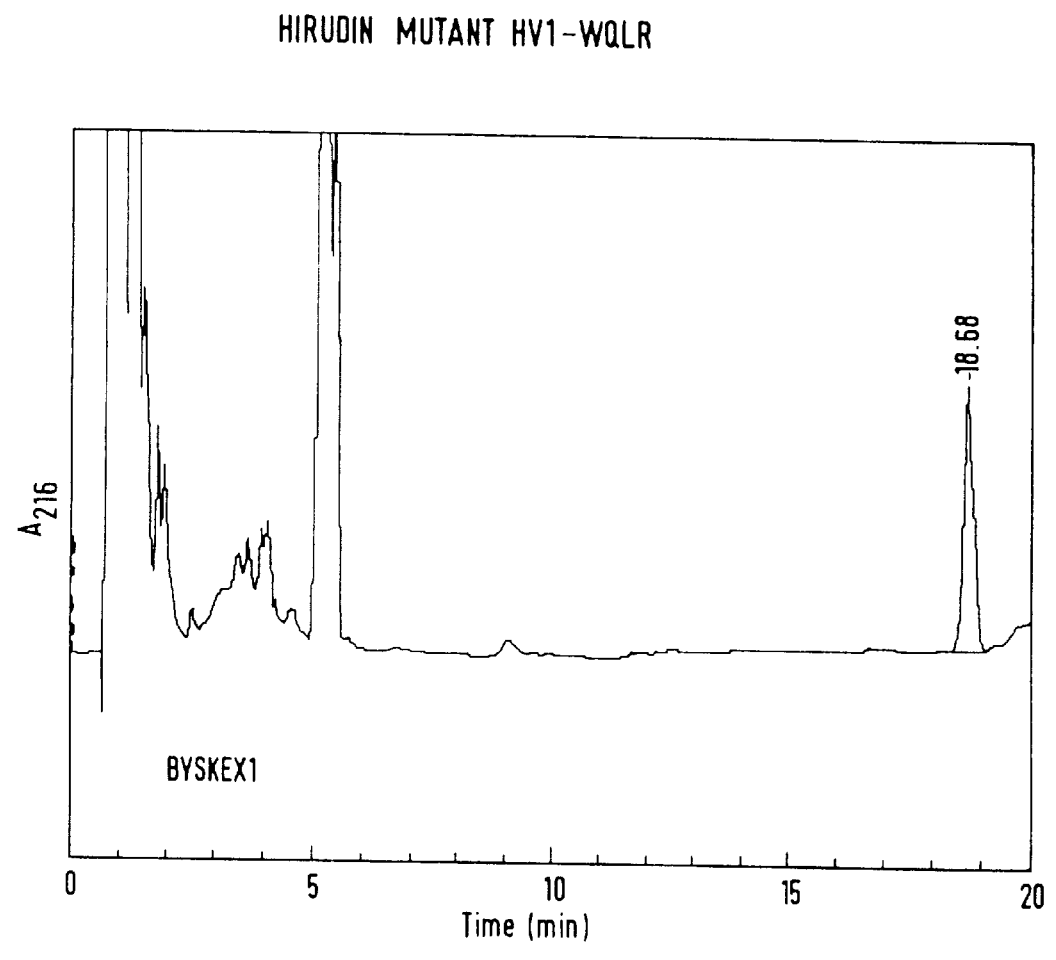
Figure 8H:
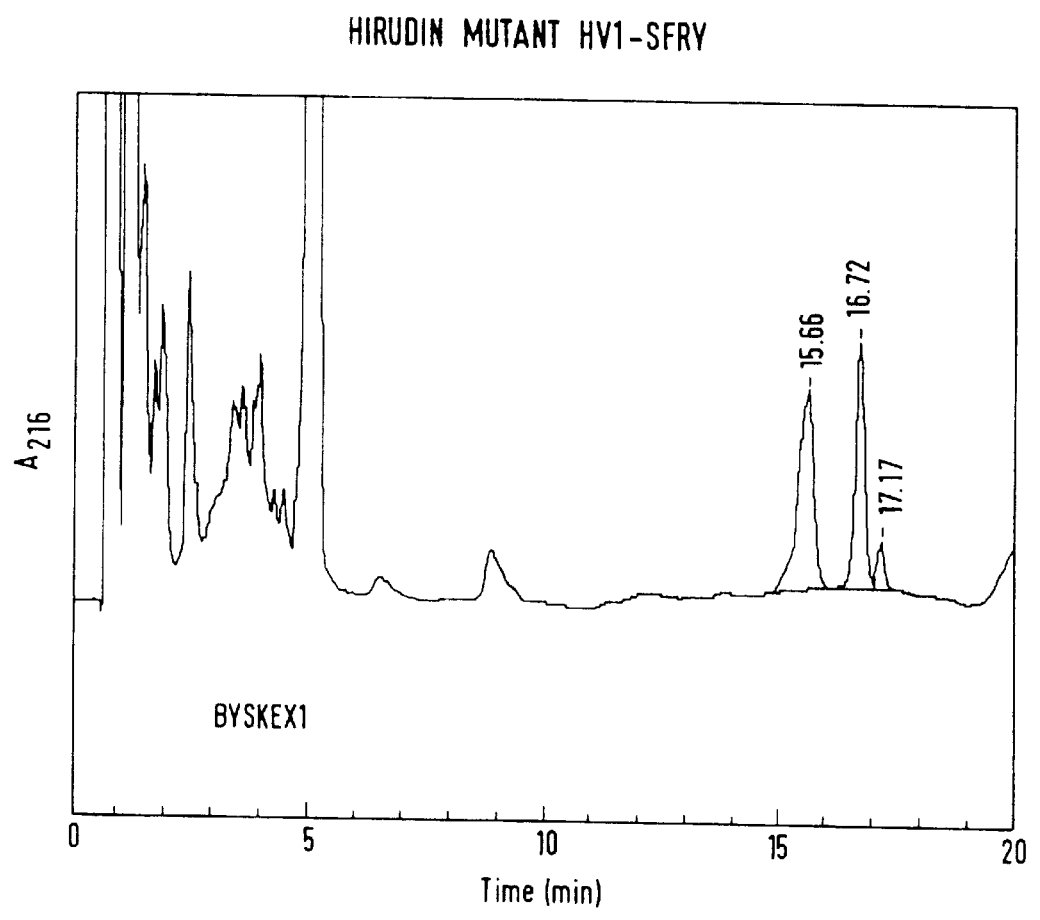

FIGS. 8A–8H depicts chromatographs of wild-type hirudin and hirudin mutants HV1-KR, HV1-WQLR and HV1-SFRY from cultures of S. cerevisiae BYSKEX1 and BYSkex1.

EXAMPLE 1

Figure 1A:
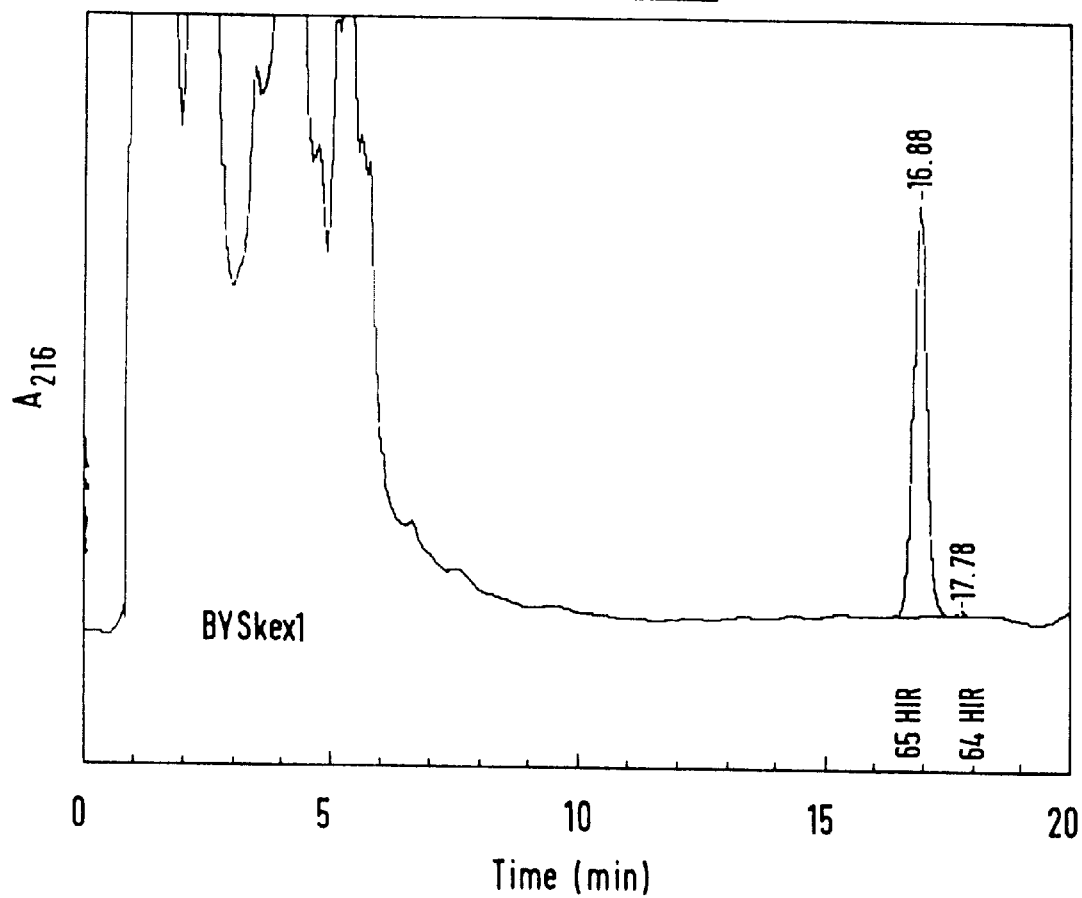
FIGS. 1A–1B depicts chromatographs of desulphatohirudins harvested from transformed KEX1 and kex1 strains of *S. cerevisiae*.

Crossing of S. cerevisiae kex1 Mutant Strain 96 with S. cerevisiae Strain BYS and Analysis of the Spores on α-factor Secretory Capacity and Carboxypeptidase yscα (KEX1 gene) Activity The S. cerevisiae kex1 mutant strain 96 (a, kex1, ade2, thr1), which is obtained from the yeast Genetic Stock Center, Berkeley, USA, is crossed into S. cerevisiae strain BYS232-31-42 (α, prb1-1, prc1-1, cps1-3, lys2, leu2, his7) [Achstetter, T. and Wolf, D. H. (1985) EMBO J. 4, 173–177; Wolf, D. H. and Ehmann, C. (1981) J. Bacteriol. 147, 418–426] carrying the wild-type KEX1 allele. Diploid heterozygous cells of the genotype kex1/KEX1 are isolated from this cross. The tetrads which derive from the diploid cells are dissected according to standard genetic techniques [Hawthorne, D. C. and Mortimer, R. K. (1960) Genetics 45, 1085–1110; Methods in Yeast Genetics 1986 (Sherman, F. et al., eds.) Cold Spring Harbor Laboratory, N.Y.].

The four spores of each tetrad are tested for their ability to secrete α-factor. To distinguish between KEX1 wild-type and kex1 mutant colonies, the pheromone-supersensitive tester strain S. cerevisiae RC629 (a, sst-2, ade2-1, ura1, his6, met1, can1, cyh2, rme) is used [Chan, R. K. and Otte, C. K. (1982) Mol. Cell. Biol. 2, 11–20; Chan, R. K. and Otte, C. K. (1982) Mol. Cell. Biol. 2, 21–29]. As expected from traits coded for by single nuclear genes, from all tetrads analysed, two spores of each tetrad secrete the a-factor, whereas the two other spores secrete α-factor. Wild-type KEX1 colonies of the α-mating type inhibit growth of the tester strain to a large extent and thus produce a large halo around themselves, since they are able to process the α-factor precursor completely and produce four active α-factor molecules from one precursor molecule. In contrast, kex1 mutant colonies inhibit the growth of the tester strain to a less extent and thus produce a small halo around themselves, since they are only able to produce one mature α-factor molecule from one precursor molecule.

The spores of several complete tetrads which are identified as defective at the kex1 gene by the above described pheromone assay, are finally tested for specific activity of carboxypeptidase yscα. Cells are grown, membranes thereof are prepared and tested for carboxypeptidase yscα activity using Cbz-Tyr-Lys-Arg as substrate as described [Wagner, J. C. and Wolf, D. H. (1987) FEBS Lett. 221, 2, 423–426]. The fact that activity of carboxypeptidase yscα is lacking in kex1 mutant cells, indicates that KEX1 is the structural gene of this enzyme. This implies that carboxypeptidase yscα is indeed involved in carboxy-terminal processing of α-factor.

EXAMPLE 2

Classification of Confirmed kex1 Mutants on Additional Deficiency of Proteases yscB, yscY and yscS S. cerevisiae kex1 mutants are classified with regard to the deficiency of other proteases (proteinase yscB, carboxypeptidase yscY and carboxypeptidase yscS) and additional growth factor requirements.

Cell material of kex1 mutants which are prepared from stationary phase in YPD (Difco) medium is suspended in the 200 µl 20 mM Tris-HCl buffer, pH 7.2 in Eppendorf microfuge and glass beads (0.4 mm in diameter) are added up to two thirds of the volume. The suspension is heavily shaken three times for 1 min on a vortex mixer with intermittent cooling on ice.

Centrifugation for 5 min allows recovery of the supernatant crude extracts. These extracts are dialysed against 0.1 M imidazole-HCl buffer pH 5.2 with 0.1 mM $ZnCl_2$ in order to activate proteases and to remove free amino acids from the extracts.

Proteinase yscB activities are measured according to the Azocoll-test [R. E. Ulane et al. (1976) J. Biol. Chem. 251, 3367; E. Cabib et al. (1973) Biochem. Biophys. Res. Commun. 50, 186; T. Saheki et al. (1974) Eur. J. Biochem. 42, 621]. After the protein concentration measurements, an aliquot of each sample is filled with 0.1 M sodium phosphate (NaPi) buffer pH 7.0 up to 100 µl to adjust the required equal protein amounts. To the protein solution, a suspension of 500 µl Azocoll (240 mg in 10 ml 0.1 M NaPi buffer, pH 7.0) is added. These mixtures are incubated at 30° C. for one hour with agitation. After the addition of 500 µl 10% trichloroacetic acid which stops the reaction, the mixtures are centrifuged two times and the absorption spectra of the supernatants at 520 nm are measured.

The activities of carboxypeptidase yscY and yscS are measured using the chromogenic substrate Cbz-Gln-Leu [cf. D. H. Wolf et al. (1978) FEBS Lett. 91, 59; D. H. Wolf et al. (1977) Eur. J. Biochem. 73, 553]. The dialysed extracts are divided into three portions and to two of them phenylmethylsulfonyl fluoride (PMSF) at a final concentration of 1 mM or EDTA at a final concentration of 5 mM is added to block the two protease activities selectively. Namely PMSF inhibits carboxypeptidase yscY activity and EDTA inhibits that of carboxypeptidase yscS. The mixtures with inhibitors are each incubated at 25° C. for an hour to complete the inhibition. After the determination of the protein concentration, two aliquots with inhibitor and one aliquot without inhibitor as a control of each sample are filled with 0.1 M NaPi buffer pH 7.4 up to 50 µl in order to receive equal protein amounts. To these protein solutions the following test solutions are added.

| | |
|---|---|
| 500 µl test solution I: | |
| L-amino acid oxidase | 0.24 mg/ml |
| horseradish peroxidase | 0.40 mg/ml |
| 0.01 mM $MnCl_2$ | |
| in 0.1 M NaPi buffer, pH 7.4 | |
| 50 µl test solution II | |
| o-dianisidin | 2 mg/ml |
| in water | |
| 500 µl test solution III | |
| 20 mM Cbz-Gly-Leu | |
| in 0.2 M potassium phosphate buffer, pH 7.4 | |

The mixtures are incubated at 28° C. for one hour and after the addition of 100 µl 20% Triton X-100 to stop the reaction, the absorbances at 405 nm are measured.

For the purpose of the subsequent transformation, an amino acid auxotrophic marker for leucine is scored with the replica-technique on minimal plates supplied with adenine, threonine, lysine and histidine, and with or without leucine.

By means of the above described assays, mutants are isolated designated S. cerevisiae BYSkex1, which exhibit a quadruple protease-deficiency ($\alpha$, prb-1, prc-1, cps-3, kex1) and an additional requirement for leucine.

EXAMPLE 3
Transformation of Saccharomyces cerevisiae Quadruple Protease Deficient Mutant The plasmid pJDB207/PHO5-HIR [European Patent Application no. 225 633] is introduced into the quadruple protease deficient mutant BYSkex1 ($\alpha$, prb-1, prc-1, cps-3, kex-1, leu2) and into KEX1 wild-type strain BYS232-31-42 ($\alpha$, prb-1, prc-1, cps-3, lys2, leu2, his7) as a control using the transformation protocol described by Hinnen et al [Proc. Natl. Acad. Sci. USA 75, 1929 (1978)].

The two different yeast strains are harvested from the early logarithmic stage in the 100 ml YPD medium ($OD_{600}$=0.2), washed with 25 ml 0.8 M sorbitol and resuspended in 5 ml of the same sorbitol solution. To these 5 ml cell suspensions, 30 $\mu$l zymolyase (ZYMOLYASE-100 T from Arthrobacter luteus, Seikagaku Kogyo Co., LTD; 10 mg/ml in 0.8 M sorbitol) are added. These mixtures are each gently agitated in 100 ml shake flasks on the shaker (110 revs/min) at 30° C. for about 30 min. At 5 min intervals a 100 $\mu$l aliquot is taken out, diluted in 10 ml distilled water and the absorbances of the dilutes at 600 nm are measured to control the progressive course of spheroplasting. To get a good spheroplast formation, the difference in absorbance before and after the treatment with zymolyase must be greater than a factor of 10. The spheroplasted cells are washed with 0.8 M sorbitol twice, resuspended in 25 ml medium HE 30 (2 M sorbitol in YPD medium) and incubated in a 100 ml shake flask with gentle agitation on the shaker (110 revs/min) at 30° C. for one hour. The cells are centrifuged (3000 rpm, 5 min), and resuspended in 1 ml HE 31 solution (10 mM Tris-HCl, pH 7.5, 10 mM $CaCl_2$, 0.9 M sorbitol) with care. To these 100 $\mu$l cell suspensions 4 $\mu$g plasmid DNAs are added. The mixture is incubated for 15 min at room temperature. 1 ml 20% polyethyleneglycole (PEG) 4000 is added to each tube and incubated for additional 30 min by room temperature, centrifuged (3000 rpm, 3 min) and resuspended in 500 $\mu$l 0.8 M sorbitol. The spheroplasts with DNA are mixed with 10 ml regeneration agar (1 M mannitol, 6.8 g/l yeast nitrogen base w/o AA (Difco), 10 g/l L-asparagine, 1.0 g/l L-histidine, 1.0 g/l adenine, 1.0 g/l threonine, 1.0 g/l lysine and 3% agar) and poured as an overlayer to plates containing a basic agar layer of the same composition. The plates are incubated at 30° C. for 96 hours until the transformant colonies appear.

A single transformed yeast colony is picked and grown in yeast synthetic minimal medium (8.4 g/l yeast nitrogen base w/o AA, 10 g/l L-asparagine and 1.0 g/l L-histidine) supplied with adenine, threonine, lysine and histidine but without leucine. The colony from the quadruple protease deficient mutant BYSkex1 and that from the triple protease deficient control strain BYSKEX1 are referred to as Saccharomyces cerevisiae BYSkex1/pJDB207/PHO5-HIR and Saccharomyces cerevisiae BYSKEX1/pJDB207/PHO5-HIR, respectively.

EXAMPLE 4
Cultivation of Saccharomyces cerevisiae Transformants with pJDB207/PHO5-HIR Cells of Saccharomyces cerevisiae transformants BYSkex1/pJDB207/PHO-HIR and BYSKEX1/pJDB207/PHO5-HIR are agitated as preculture in 10 ml of yeast complete medium HE 41 [4.5 g/l casamino acids, 4 g/l yeast extract, 20 g/l saccharose, 20 g/l glucose, 3.6 g/l $(NH_4)_2SO_4$, 0.2 g/l $MgSO_4.7H_2O$, 0.013 g/l $CaCl_2.H_2O$ and 1 ml/l trace elements mixture (10 g/l $FeSO_4.7H_2O$, 50 g/l $ZnSO_4.7H_2O$, 3.3 g/l $CuSO_4.5H_2O$, 3 g/l $MnSO_4.H_2O$, 2 g/l $CoCl_2.6H_2O$ and 1 g/l $(NH_4)_6Mo_7O_{24}.4H_2O$)] at 28° C. and cultivated for about 48 hours until they reach the stationary phase. The harvested cells are washed in 0.9% NaCl. 50 ml of the above described yeast synthetic medium are inoculated with a 5% inoculum. The cultures are inoculated up to a cell density of $OD_{600}$=0.3 and agitated at 28° C. for up to 72 hours at 250 revs/min.

Yeast complete medium HE 41 is used in order to remove the background absorption in HPLC analysis.

EXAMPLE 5
Analytics of Hirudin-65 and its Carboxy-Terminal Degradation Products Hirudin-64 and Hirudin-63 from Fermentation Cultures of Saccharomyces cerevisiae Transformants BYSkex1/pJDB207/PHO5-HIR and BYSKEX1/pJDB207/PHO5-HIR using Reversed Phase HPLC Samples from liquid yeast cultures are prepared by centrifugation to produce a clear solution which is diluted 1:10 (v/v) with acetic acid (1M) and are subjected to HPLC analysis under following conditions.

A HIBAR (MERCK) column (4×125 mm) is filled with reversed phase, wide pore silica material (type 71252, 300-5-C18, MACHEREY-NAGEL), a spherical stationary phase with a particle diameter of 5 $\mu$m and a porosity of 300 A. The column endings are equipped with stainless steel frits. Mobile phase A is made from water (Nanopure®, BARNSTEAD) containing 0.1% (v/v) trifluoroacetic acid. Mobile phase B is made from 20% of mobile phase A and 80% (v/v) of acetonitrile (HPLC-grade, FLUKA) containing 0.08% (v/v) of trifluoroacetic acid.

Chromatographic separations are performed at a flow rate of 1.5 ml/min running the following gradient and the eluents are monitored by absorbance at 216 nm.

| t(min) | % A | % B |
|--------|-----|-----|
| 0 | 90 | 10 |
| 1 | 79 | 21 |
| 9 | 79 | 21 |
| 17 | 67 | 33 |
| 20 | 0 | 100 |
| 22 | 0 | 100 |
| 24 | 90 | 10 |
| 32/0 | 90 | 10 |

A standard solution for the calibration of the system is made by dissolving 1 mg of pure desulphatohirudin in 1 ml water. 50 $\mu$l of this standard solution are injected onto the column and chromatographed as described to calibrate the system.

Figure 1B:
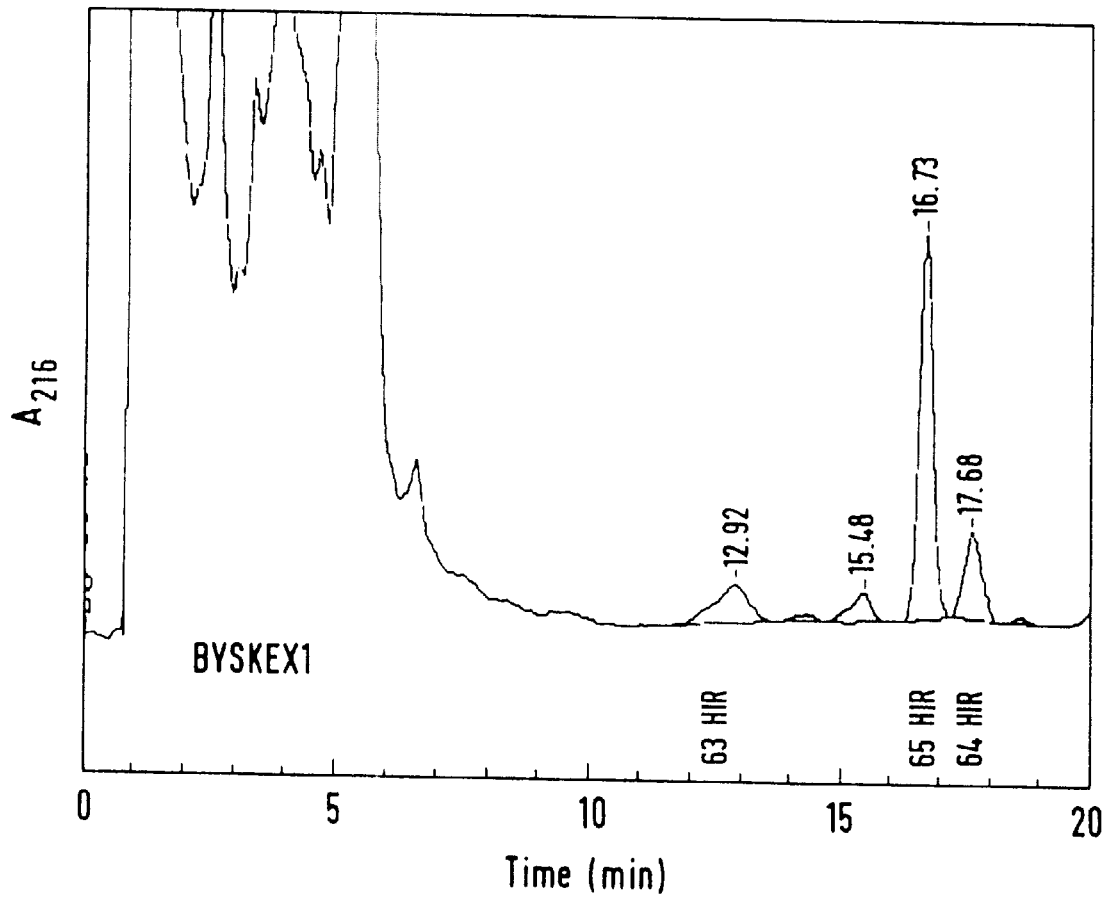
Figure 8A:
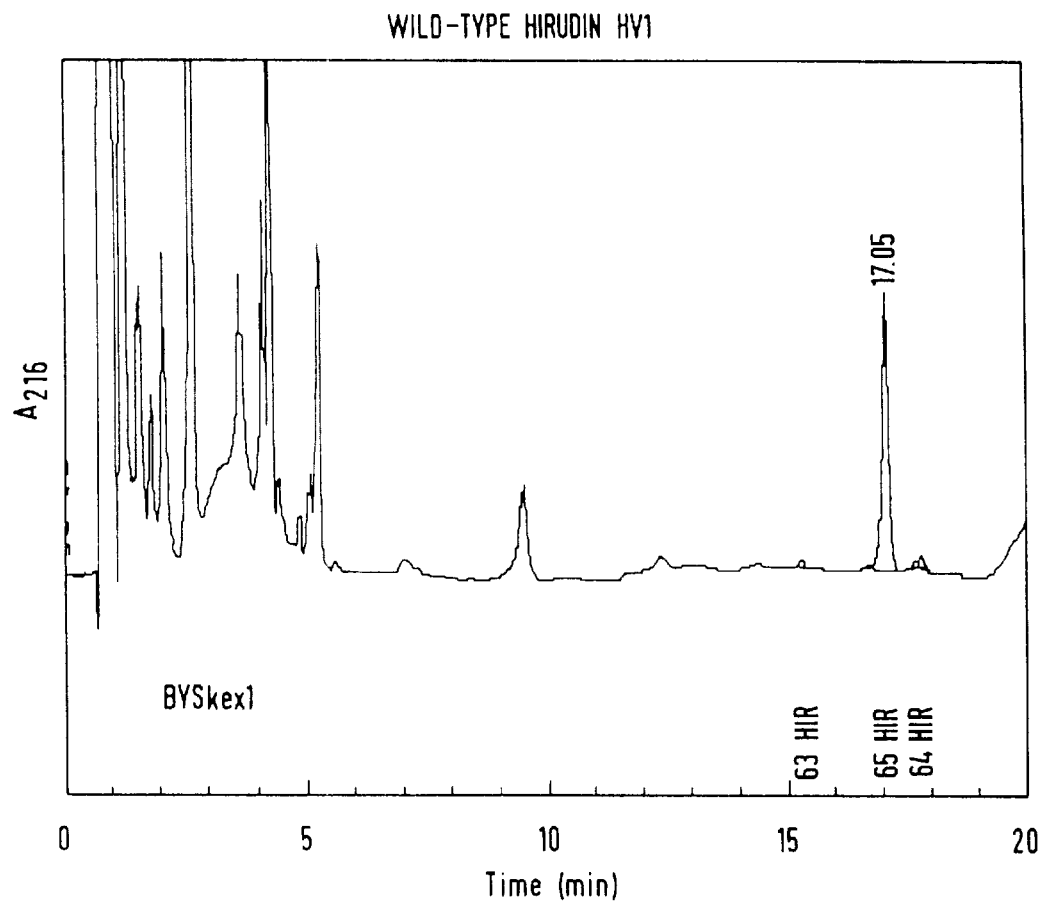
Figure 8B:
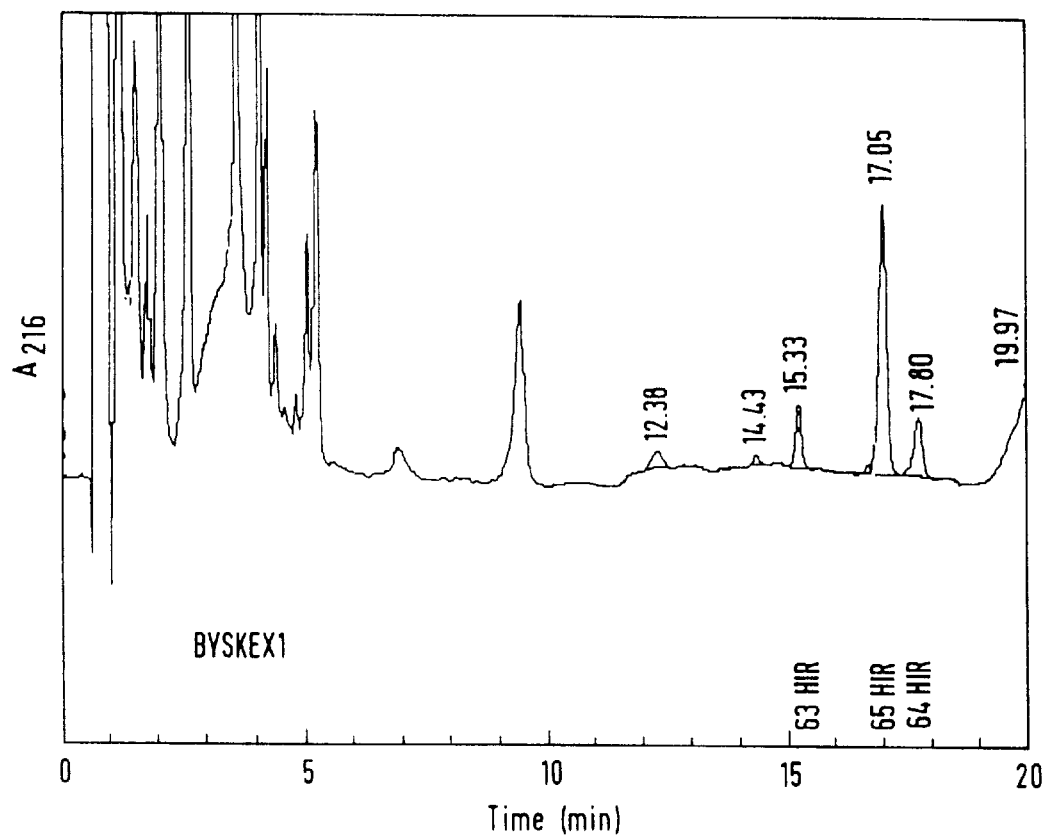
Figure 8C:
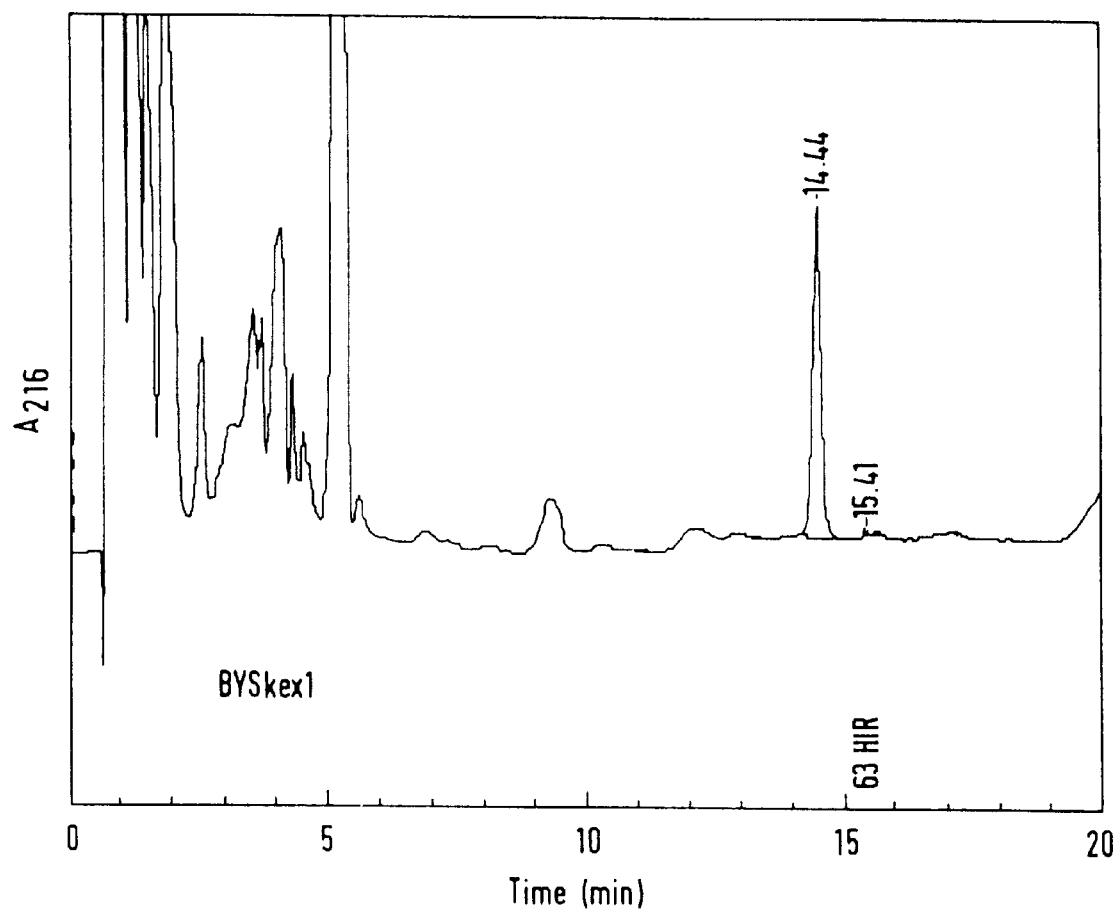
Figure 8D:
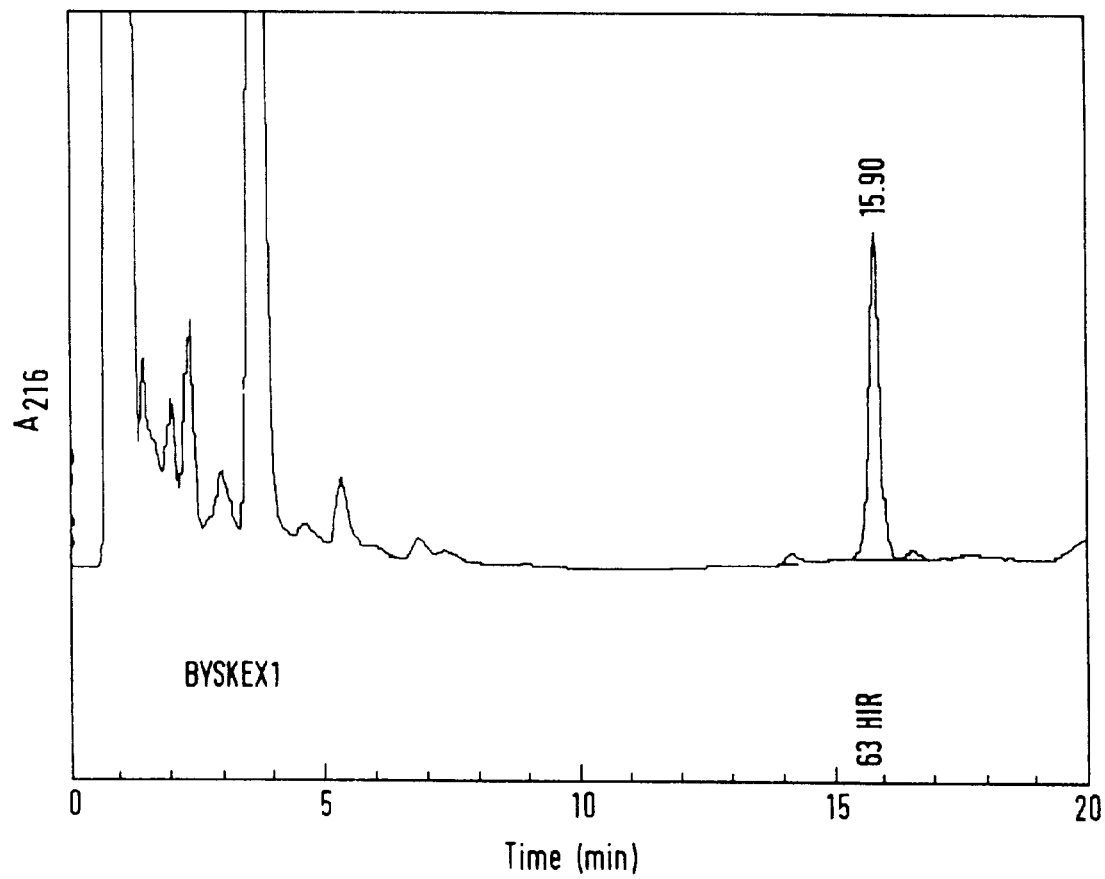

In FIG. 1, analytical reversed phase liquid chromatographs of hirudins harvested from S. cerevisiae BYSkex1/pJDB207/PHO5-HIR and S. cerevisiae BYSKEX1/pJDB207/PHO5-HIR cultures are shown. The chromatographic conditions are the same as described above. It is evident that, contrary to strain BYSKEX1/pJDB207/PHO5-HIR, the peptidase ysc$\alpha$ negative strain BYSkex1/pJDB207/PHO5-HIR produces a desulphatohirudin product ("HIR-65") which is essentially free of C-terminally shortened byproducts desulphatohirudin HIR-64 lacking the C-terminal amino acid Gln and HIR-63 lacking the C-terminal amino acids Leu and Gln.

EXAMPLE 6
In Vitro Synthesis of the Hirudin HV1 Gene with Preferred Yeast Codons The coding sequence of the hirudin expression cassette is devised with preferred yeast codons [B. Hall (1982) J. Biol. Chem. 257, 3026] to guarantee optimal translation of the hirudin mRNA. The coding sequence contains the PHO5 signal sequence fused in frame to the coding sequence of desulphatohirudin HV1. The 5' end of the synthetic DNA contains the sticky ends of the EcoRI restriction site.

At the 3' end the stop codon TAG is immediately followed by the sticky ends of the BamHI site. The sequence of the 257 bp EcoRI-BamHI DNA fragment is shown in FIG. 2.

FIG. 2 also indicates the strategy for the in vitro synthesis of the double-stranded DNA fragment. 21 oligodeoxynucleotides are synthesized using the phosphor-amidite method [M. H. Caruthers, in: Chemical and Enzymatic Synthesis of Gene Fragments (H. G. Gassen and A. Lang, Eds.), Verlag Chemie, Weinheim, FRG (1982)] on an Applied Biosystems Model 380B synthesizer. The sequence of the individual oligonucleotides is shown in FIG. 2. The overlaps are unique. The lyophilized oligonucleotides are redissolved in 50 mM Tris-HCl pH 8.0 at a concentration of 10 pmoles/$\mu$l. The 21 oligonucleotides are allocated to two groups; [A] No. 1-11 representing the 5' half of the DNA fragment, [B] No. 12-21 for the 3' half. The 2 groups are treated separately. 10 pmoles each of the oligonucleotides of a group are mixed. The oligos are phosphorylated in 20 $\mu$l of 25 mM Tris-HCl pH 8.0, 10 mM MgCl$_2$, 10 mM NaCl, 3 mM DTT, 0.4 mM ATP and 8 units of polynucleotide kinase (Boehringer) for 1 h at 37° C. After 30 min at room temperature both mixtures (A and B) are each heated for 5 min at 95° C. in a waterbath. The samples are allowed to cool slowly to room temperature in the waterbath overnight. The annealed oligonucleotide mixtures A and B are then stored on ice.

Plasmid pBR322 is cut to completion with EcoRI and BamHI. The large, 4 kb fragment is isolated on a preparative 0.6% agarose gel. The DNA is recovered by electroelution, purified by DE52 ion exchange chromatography and ethanol precipitation as described in Example 7. The DNA is redissolved in H$_2$O at a concentration of 0.4 pmoles/$\mu$l.

10 $\mu$l of the annealed oligonucleotide mixture A (5 pmoles each of oligos 1–11), 9.5 $\mu$l of mixture B (5 pmoles each of oligos 12–21), 0.4 pmoles of the 4 kb EcoRI-BamHI fragment of pBR322 and 400 units of T4 DNA ligase (Biolabs) are incubated for 16 h at 15° C.

10 $\mu$l aliquots are used to transform competent E. coli HB 101 Ca$^{++}$ cells. 12 transformed, ampicillin resistant colonies are grown individually in LB medium containing 100 $\mu$g/ml of ampicillin. Plasmid DNA is prepared by the method of Holmes et al. [Anal. Biochem. 114, 193 (1981)] and analysed by EcoRI and BamHI restriction digests. Plasmid DNAs with the 257 bp EcoRI-BamHI insert are further analysed by DNA sequencing on both strands. Oligonucleotides 3, 11, 12, 14 and 20 (see FIG. 2) are used as sequencing primers. One clone with a correct sequence on both DNA strands is selected and referred to as pBR322/YHIR.

EXAMPLE 7
Construction of Plasmid pJDB207/GAPFL-YHIR pJDB207/GAPFL-YHIR is a yeast plasmid for the expression of desulphatohirudin variant HV1 under the control of a short, constitutive promoter of the yeast glyceraldehyd-3-phosphate dehydrogenase (GAPDH) gene. The coding sequence of desulphatohirudin consists of preferred yeast codons.

10 $\mu$g of plasmid pBR322/YHIR are digested with restriction endonucleases BamHI and EcoRI. The 257 bp EcoRI-BamHI fragment is separated from other DNA fragments on a 1.2% preparative agarose gel. The DNA bands are stained by ethidiumbromide and visualized under UV light at 360 nm. The 257 bp DNA band is cut from the gel and electroeluted in 0.2×TBE buffer (TBE: 90 mM Tris-base, 90 mM boric acid, 2.5 mM EDTA, pH 8.3) for 45 min at 100 mA. After changing polarity for 45 sec, the DNA solution is collected and adjusted to 0.15 M NaCl. The DNA is adsorbed to a 100 $\mu$l bed of DE52 ion exchanger (Whatman) and eluted in 400 $\mu$l of high salt buffer (10 mM Tris-HCl pH 8.0, 1 mM EDTA, 1.5 M NaCl). The DNA is ethanol precipitated and resuspended in H$_2$O at a concentration of 0.1 pmoles/$\mu$l.

Plasmid pJDB207/GAPFL-HIR [European Patent Application No. 225 633] contains the synthetic gene for desulphatohirudin (based on the E. coli codon usage) fused in frame to the signal sequence of yeast acid phosphatase (PHO5). The gene is expressed under the control of a short constitutive glyceraldehyd-3-phosphate dehydrogenase (GAPFL) promoter of yeast on shuttle vector pJDB207. 10 $\mu$g of plasmid pJDB207/GAPFL-HIR are digested with SalI and EcoRI. The 478 bp SalI-EcoRI fragment contains the Sal-Bam pBR322 part and the GAPFL promoter. The DNA fragment is isolated on a 0.8% preparative agarose gel, electroeluted and purified by DE52 chromatography and ethanol precipitation. The DNA is resuspended in H$_2$O at a concentration of 0.1 pmoles/$\mu$l. 5 $\mu$g of pJDB207/GAPFL-HIR are digested with SalI and BamH. The large 6.7 kb vector fragment is isolated as described above.

0.2 pmoles of the 478 bp SalI-EcoRI promoter fragment, 0.2 pmoles of the 257 bp EcoRI-BamHI fragment containing the PHO5 signal sequence and the synthetic hirudin gene (yeast codons) and 0.1 pmoles of the 6.7 kb vector fragment are ligated in 10 $\mu$l of 60 mM Tris-HCl pH 7.5, 10 mM MgCl$_2$, 5 mM DTT, 1 mM ATP and 200 units of T4 DNA ligase (Biolabs) for 6 h at 15° C. A one $\mu$l aliquot of the ligation mixture is used to transform competent E. coli HB 101 cells.

12 transformed, ampicillin resistant colonies are grown individually in LB medium containing 100 $\mu$g/ml of ampicillin. Plasmid DNA is prepared by the method of Holmes et al. (supra) and analysed by SalI/HindIII double digests. A single clone with the expected restriction pattern is referred to as pJDB207/GAPFL-YHIR.

In an analogous manner the construction can be performed with a 543 bp SalI-EcoRI promoter fragment of plasmid pJDB207/GAPEL-HIR [European Patent Application No. 225 633]. The resulting new plasmid is referred to as pJDB207/GAPEL-YHIR.

EXAMPLE 8
Construction of Plasmid pJDB207/PHO5(−173)-HIR pJDB207/PHO5(−173)-HIR is a yeast plasmid for the expression of desulphatohirudin variant HV1 under the control of a short PHO5 promoter. The PHO5(−173) promoter element comprises the nucleotide sequence of the yeast PHO5 promoter from position −9 to −173 (BstEII restriction site), but has no upstream regulatory sequences (UAS). The PHO5(−173) promoter therefore behaves like a constitutive promoter.

Plasmid pJDB207/PHO5(Eco)-HIR (EP 225 633) contains the full length, regulated PHO5 promoter with an EcoRI site introduced at position −8 with respect to the ATG of the PHO5 signal sequence and the coding sequence of desulphatohirudin which is followed by the PHO5 transcription termination fragment. This example describes the replacement of the regulated PHO5 promoter by the short PHO5(−173) promoter element.

20 μg of plasmid pJDB207/PHO5(Eco)-HIR are digested with BstEII. The sticky ends of the restriction fragments are filled in a reaction with Klenow DNA polymerase (1 unit/μg DNA) in 200 μl of 60 mM Tris-HCl pH 7.5, 10 mM MgCl$_2$, 0.1 mM each of dATP, dCTP, dGTP, TTP for 30 min at room temperature. After phenol extraction the DNA is ethanol precipitated.

4.16 μg of BamHI linker (5'-CGGATCCG-3', Biolabs) are phosphorylated in 100 μl of 60 mM Tris-HCl pH 7.5, 10 mM MgCl$_2$, 5 mM DTT, 0.5 mM ATP and 18 units of T4 polynucleotide kinase (Boehringer) for 45 min at 37° C. After 10 min at 75° C. the reaction mixture is slowly cooled to room temperature. The annealed oligonucleotide linkers are stored at −20° C.

4 pmoles of the [BstEII]/blunt end fragments of plasmid pJDB207/PHO5(Eco)-HIR are incubated for 16 h at 15° C. with a 100 fold excess of the phosphorylated and annealed BamHI linker in 208 μl of 60 mM Tris-HCl pH 7.5, 10 mM MgCl$_2$, 5 mM DTT, 3.5 mM ATP and 800 units of T4 DNA ligase (Biolabs). After inactivation of the ligase for 10 min at 85° C. the excess linkers are removed by precipitation of the DNA in the presence of 10 mM EDTA, 300 mM sodium acetate pH 6.0 and 0.54 volumes of isopropanol. The DNA is digested with BamHI and EcoRI. The DNA fragments are separated on a 0.8% preparative agarose gel. The 172 bp BamHI-EcoRI promoter fragment is recovered from the gel by electroelution and ethanol precipitation. The DNA is resuspended at a concentration of 0.1 pmoles/μl.

Plasmid pJDB207/PHO5(Eco)-HIR is digested with EcoRI and HindIII. The 643 bp EcoRI-HindIII fragment is isolated as described above. The DNA fragment contains the PHO5 signal sequence fused in frame to the coding sequence of desulphatohirudin and the PHO5 transcription termination fragment. The plasmid is also cut with HindIII and BamHI. The 6.6 kb vector fragment is isolated.

0.2 pmoles each of the 172 bp BamHI-EcoRI fragment and the 643 bp EcoRI-HindIII fragment and 0.1 pmoles of the 6.6 kb vector fragment are ligated in 10 μl of 60 mM Tris-HCl pH 7.5, 10 mM MgCl$_2$, 5 mM DTT, 1 mM ATP and 400 units of T4 DNA ligase (Biolabs) for 6 h at 15° C. A one μl aliquot of the ligation mixture is added to 100 μl of calcium-treated, transformation-competent E. coli HB101 cells.

12 transformed, ampicillin resistant colonies are grown in LB medium containing 100 μg/ml of ampicillin. Plasmid DNA is prepared and analysed by BamHI and SalI/HindIII digests. One clone with the expected restriction fragments is selected and referred to as pJDB207/PHO5(−173)-HIR.

EXAMPLE 9
Construction of plasmid pDP34

Yeast 2 micron covalently closed circle DNA is isolated from Saccharomyces cerevisiae strain S288C. Cells are incubated with 5 μg/ml of Zymolyase (100,000 units/μg) for 20 min at 37° C. to digest the cell walls. The spheroplasts are lysed with 2% SDS. EDTA is then added to 25 mM, ethidium bromide to 1 mg/ml and caesium chloride to a final density of 1.55 g/ml. Plasmid DNA is separated from the chromosomal DNA by ultracentrifugation for 42 hours at 42,000 rpm at 15° C. The 2 micron plasmid DNA is cut from the gradient with a syringe. The ethidium bromide is removed by extraction with NaCl-saturated isopropanol and the plasmid DNA is finally ethanol precipitated. The purified two-micron plasmid DNA is then linearised with PstI and cloned into the PstI site of pUC19 [J. Norrander et al., Gene 26 (1983), 101] to give plasmid pDP31.

Plasmid pJDB207 is digested with the restriction enzymes KpnI and HpaI. The resulting 0.55 kb HpaI-KpnI fragment contains the junction between the 2 micron sequence and the defective promoter of the dLEU2 gene.

Plasmid pUC7/LEU2 contains the yeast genomic 2.2 kb XhoI-SalI fragment of the LEU2 gene [A. Andreadis et al. (1982) Cell 31, 319] cloned into the SalI site of the plasmid pUC7 [J. Vieira et al. (1982) Gene 19, 259]. Plasmid pUC7/LEU2 is cut with KpnI and HpaI. The 4.25 kb KpnI-HpaI fragment is ligated to the 0.55 kb HpaI-KpnI fragment of pJDB207. This results in plasmid pDP30 where the original two micron/dLEU2 fusion as in plasmid pJDB207 is placed in front of the LEU2 gene with its complete terminator. pDP30 is digested with HpaI and SalI and the 1.85 kb fragment containing the complete LEU2 gene is purified and cloned into the 8.7 kb SalI-HpaI fragment of plasmid pDP31. The resulting plasmid, pDP33 (see FIG. 3), is linearised by partial digestion with HindIII in the presence of 50 μg/ml ethidium bromide [M. Oesterlund et al. (1982) Gene 20, 121] and ligated with the 1.17 kb HindIII fragment containing the URA3 gene [M. Rose et al. (1984) Gene 29, 113]. Insertion of the URA3 gene is selected for by transformation into the E. coli strain pyrF [M. Rose et al., supra]. A positive clone is referred to as plasmid pDP34 (see FIG. 4).

pDP34 is a yeast-E. coli shuttle vector with the ampicillin resistance marker for E. coli and the URA3 and dLEU2 yeast selective markers. It contains the complete 2 micron sequence in the A form and is REP1, REP2 and FLP proficient.

EXAMPLE 10
Cloning of Hirudin Expression Cassettes into pDP34

Plasmid pDP34 is digested with BamHI. The sticky ends of the restriction site are filled in a reaction with Klenow DNA polymerase (T. Maniatis et al., in: "Molecular Cloning. A Laboratory Manual", Cold Spring Harbor Laboratory, 1982). The DNA is further cut with SalI and the 11.8 kb vector fragment is isolated on a preparative 0.6% agarose gel. The DNA is recovered by electroelution and ethanol precipitation. Different expression cassettes are cloned into the pDP34 vector fragment between the SalI and [BamHI]/ blunt end sites.

Plasmid pJDB207/GAPFL-YHIR is digested with HindIII. The sticky ends are converted to blunt ends by Klenow DNA polymerase. The DNA is ethanol precipitated and further digested with SalI. The 1.1 kb SalI-[HindIII]/blunt end fragment contains the complete expression cassette with pBR322 sequences, the GAPFL promoter, the PHO5 signal sequence fused in frame to the coding sequence (preferred yeast codons) of desulphatohirudin and the PHO5 transcription termination fragment. The 1.1 kb fragment is isolated on a preparative 0.8% agarose gel, recovered from the gel by electroelution and purified by DE52 ion exchange chromatography and ethanol precipitation. 0.2 pmoles of the 1.1 kb fragment and 0.1 pmoles of the 11.8 kb vector fragment are ligated in 10 μl of 60 mM Tris-HCl pH 7.5, 10 mM MgCl$_2$, 5 mM DTT, 3.5 mM ATP and 400 units of T4 DNA ligase (Biolabs) for 16 h at 15° C. A one μl aliquot is used to transform E. coli HB101 Ca$^{2+}$ cells. 5 transformed, ampicillin resistant colonies are analysed. Plasmid DNA is digested with BamHI and SalI/BamHI. One clone with the correct restriction fragments is selected and referred to as pDP34/GAPFL-YHIR (see FIG. 5).

In an analogous manner the 1.2 kb SalI-[HindIII]/blunt end fragment of pJDB207/GAPEL-YHIR (see Example 7) is cloned into the pDP34 vector, which results in plasmid pDP34/GAPEL-YHIR.

Plasmid pJDB207/PHO5(−173Y-HIR is digested with SalI and EcoRI. The 448 bp SalI-EcoRI fragment is isolated as described. The DNA fragment contains the SalI-BamHI part of pBR322 and the short constitutive PHO5(−173)-promoter (see Example 8). Plasmid pJDB207/GAPFL-YHIR is digested with HindIII. The sticky ends are converted to blunt ends by Klenow DNA polymerase. The DNA is further digested with EcoRI. The 642 bp EcoRI-[HindIII]/blunt end fragment is isolated. It contains the PHO5 signal sequence, the coding sequence of desulphatohirudin (with preferred yeast codons) and the PHO5 transcription termination fragment. 0.2 pmoles each of the 448 bp SalI-EcoRI fragment and the 642 bp EcoRI-blunt end fragment and 0.1 pmoles of the 11.8 kb SalI-[BamHI]/blunt end vector fragment are ligated. Aliquots of the ligation mixture are used to transform E. coli HB 101 Ca$^{++}$ cells. Plasmid DNA of 12 transformants is analysed by BamHI and SalI/BamHI digests. One clone with the correct plasmid is selected and referred to as pDP34/PHO5(−173)-YHIR (see FIG. 6).

EXAMPLE 11
Further Expression Plasmids for the Hirudin Gene with E. coli Codons Expression plasmids containing the synthetic gene for desulphatohirudin variant HV1 based on the E. coli codon usage are constructed in a way analogous to the description in Example 10. The 1.1 kb SalI-[HindIII]/blunt end fragment of pJDB207/GAPFL-HIR (European Patent Application No. 225 633) is isolated and cloned into vector pDP34. The resulting expression plasmid is pDP34/GAPFL-HIR comprising the synthetic gene for desulphatohirudin based on preferred E. coli codons expressed under the control of the constitutive GAPFL promoter.

For a similar construction the 1.1 kb SalI-[HindIII]/blunt end fragment of pJDB207/PHO5(−173)-HIR (see Example 8) is cloned into pDP34. The resulting plasmid pDP34/PHO5(−173)-HIR contains the synthetic gene for desulphatohirudin (E. coli codons) under the control of the short constitutive PHO5(−173) promoter.

EXAMPLE 12
The Hirudin Expression Cassette Cloned into Plasmid pDP92

Vectors containing the complete two-micron sequence do not necessarily express all the functions of the genuine yeast two-micron circle. Open reading frames can be destroyed by cloning. Since no function had been known so far for the gene product of the "D" reading frame the unique PstI site withing this gene was used for cloning the dLEU2 gene [Beggs, J. D. (1978) Nature 275, 104–109] or inserting the pUC19 vector part as in plasmid pDP31 (see Example 9). Only recently it was suggested that the D gene product regulates expression of the FLP gene product [J. A. H. Murray et al. (1987) EMBO J. 6, 4205)]. To take full advantage of the two-micron circle a vector is constructed which is proficient for all the known two-micron functions including the D gene product.

a) Construction of plasmid pDP92 (see FIG. 7)

Plasmid pDP31 (Example 9) is digested with PstI and HpaI resulting in three fragments. Plasmid pK19 [conferring kanamycin resistance; Pridmore, R. D. (1987) Gene 56, 309–312] is linearized with SmaI. The DNA fragments of both digests are phenol extracted and precipitated with ethanol. The DNA fragments are mixed and ligated. The ligation mixture is transformed [Hanahan, D. J. (1983) Mol. Biol. 166, 557–580] into competent E. coli JM109 cells [Yanisch-Perron, C. et al. (1985) Gene 33, 103–119] expressed for 2 h at 37° C. in LB medium and then plated on LB agar plates supplemented with 50 μg/ml of kanamycin, 30 μg/ml of XGal and 7 μg/ml of IPTG.

12 white, kanamycin-resistant colonies are grown. Plasmid DNA is analysed by XbaI and BamHI/KpnI digests. A single clone which has lost the pUC19 vector part of pDP31, restored the two-micron D reading frame by religation of the PstI site and which has the pK19 plasmid blunt end inserted into the HpaI site is referred to as pDP91. The plasmid contains the large HpaI-PstI and the small PstI-HpaI fragments of two-micron plasmid cloned into the SmaI site of pK19. By religation of the PstI sites the D reading frame is reconstituted.

The URA3 gene is isolated on a 1.17 kb HindIII fragment from plasmid pDP34 (see Example 9) and cloned into the unique HindIII site of plasmid pUC12. A clone with the URA3 gene inserted in the same orientation as the ampicillin resistance gene is referred to as pUC12/URA3. Plasmid pDP91 and pUC12/URA3 are both digested with SacI and BamHI resulting in two fragments each. The DNA fragments are mix-ligated and used to transform competent E. coli JM109 cells. Cells are plated on to LB agar plates supplemented with 100 μg/ml of ampicillin, 30 μg/ml of XGal and 7 μg/ml of IPTG.

12 white, ampicillin-resistant colonies are grown. Plasmid DNA is analysed by HindIII and PvuII digests. A single clone is referred to as pDP92, comprising the complete two-micron sequence proficient for all its known functions and the URA3 gene cloned into the pUC vector.

b) Cloning of hirudin expression cassettes into pDP92

In analogy to Example 10 pDP92 is digested with BamHI. The sticky ends are filled in a reaction with Klenow DNA polymerase. The DNA is further cut with SalI. The 10.2 kb vector fragment is isolated. The 1.1 kb SalI-[HindIII]/blunt end fragment of plasmid pJDB2071GAPFL-YHIR is isolated and ligated to the vector fragment.

6 transformed, ampicillin-resistant colonies are analysed. Plasmid DNA is digested with BamHI, PstI and SalI/BamHI. One clone with the expected restriction fragments is selected and referred to as pDP92/GAPFL-YHIR. In a similar way plasmid pDP92/GAPEL-YHIR is obtained using the 1.2 kb SalI-[HindIII]/blunt end fragment of pJDB207/GAPEL-YHIR (see Example 7).

Plasmid pDP92/PHO5(−173)-YHIR is constructed as described in Example 10 using the 10.2 kb SalI-[BamHI]/blunt end pDP92 vector fragment (see above).

EXAMPLE 13
Construction of Two-Micron DNA Free Saccharomyces cerevisiae Host Strains In order to remove the endogenous two-micron plasmid, in a first step a deletion is introduced in the URA3 gene of strain HT246 (DSM 4084; α, leu 2–3, leu 2–112, prb) to make the strain auxotrophic for uracil. HT246 is transformed with 1 μg of plasmid YeP13 [Broach, J. R., Strathern, J. N., Hicks, J. B. (1979) Gene 8, 121–123] using the transformation protocol described by Hinnen et al. [Proc. Natl. Acad. Sci. USA 75, 1929 (1978)]. 10 μg of plasmid pUC12ura3Δ containing a deletion in the URA3 gene [Sengstag, Ch., Hinnen, A. (1987) Nucleic Acids Research 15, 233–246] are added along with plasmid YEP13. Roughly 3000 leucine prototrophic transformants are resuspended in 5 ml minimal medium (Difco Yeast Nitrogen Base without amino acids to which 2% glucose, 0.1% leucine, 0.1% uracil and 0.25% fluoroorotic acid are added) in a small shake flask and incubated for 60 hours at 30° C. and 180 r.p.m. Transformants which grow are resistant to the toxic analogue fluoroorotic acid and carry therefore a replacement in the chromosomal URA3 gene by ura3Δ. The grown cells are plated out on full medium composed of (g/l): Peptone 20, yeast extract 10, glucose 20, and after growth for 48 h at 30°

C. replicaplated onto minimal medium (Difco) yeast nitrogen base without amino acids. Supplemented with 2% glucose and 0.1% leucine) to detect uracil auxotrophs. Several auxotrophs are picked and tested for plasmid YEP13 loss conferring leucine auxotrophy. One individual colony (designated Tr889) requiring leucine and uracil is picked and used for further experimentation.

Tr889 is transformed with plasmid pDP38 [obtained from plasmid pDP34 by digestion with SphI and religation of the resulting 8.4 kb fragment; see FIG. 4], which carries both marker genes LEU2 and URA3 (transformation protocol, supra). Transformed yeast cells are first selected on yeast minimal media plates deficient in uracil, supplemented with leucine and then replica-plated onto minimal medium deficient in leucine and supplemented with uracil. 10 weakly growing colonies are picked and individually grown in liquid full medium (supra) over about a hundred generations. By doing so, the cells lose the pDP38 plasmid and—to a certain percentage—simultaneously also the endogenous two-micron plasmid. 10 uracil and leucine requiring colonies are picked, DNA is prepared, the DNA is digested to completion with PstI and probed with $^{32}$P-labelled yeast two-micron DNA on Southern blots. One isolate without any hybridisation signal is referred to as H449 (a, leu2–3, leu2–112, ura3Δ, prb, cir°), an isogenic two-micron free (cir°) derivative of yeast strain HT246.

EXAMPLE 14

Preparation of a kex1 variant of S. cerevisiae H449 by disruption of the genomic KEX1 gene Carboxypeptidase yscα activity is eliminated from S. cerevisiae strain H449 (prb, leu2, ura3, cir°) through disruption of the genomic KEX1 gene. For this purpose the KEX1 gene is identified in a yeast genomic library and cloned in a suitable vector. The URA3 gene, which serves as a selective marker, is inserted in the structural gene of KEX1 to disrupt its reading frame. The hybrid plasmid DNA comprising the URA3 gene flanked on either side by KEX1 sequences is introduced into the Ura⁻ yeast strain H449. The sequence homology of the KEX1 gene on the plasmid and on the chromosome allows in vivo recombination, which transforms yeast cells from Ura⁻ to Ura⁺ and concomitantly from KEX1 to kex1. Strains with a disrupted kex1 gene do not synthesize a functional yscα protein.

The gene coding for KEX1 is cloned from a yeast genomic library [in the centromere shuttle vector pCS19; Sengstag, C. et al. (1987) Nucl. Acids Res. 15, 233] by colony-hybridization with a KEX1 specific oligonucleotide probe. The sequence of the following oligonucleotide

5'-GTCGAATCCGGCCCTTTTAGGGTGAATTCA-3' is derived from the published KEX1 sequence [cf. Dmochowska, A., et al. (1987) Cell 50, 573] and selected from the whole sequence by its particular low homology to the sequence of yscY. It hybridizes to KEX1 DNA upstream of the EcoRV restriction site, which is used for insertion of the URA3 gene. The same oligonucleotide can be used as a sequencing primer for the confirmation of the URA3 fragment insertion. This synthetic oligonucleotide is radiolabelled and used to screen the gene library.

About 10,000 clones [5×2000 clones/plate (ϕ=140 mm)] are screened by colony-hybridization [cf. Woods, D. E., et al. (1982) Proc. Natl. Acad. Sci USA 79, 5661 and Whitehead A. S., et al. (1983) Proc. Natl. Acad. Sci. USA 80, 5387]. From two repeated screening procedures, 5 independent positive clones are isolated. One of them is designated pKEX1. To cut out a KEX1 specific HindIII-BamHI fragment (1380 bp), the pKEX1 plasmid DNA is digested with the corresponding two endonucleases. The respective fragment is transferred to the Bluescript vector M13+ with SK polylinker and this clone is sequenced using a universal primer for the M13 vector to confirm the KEX1 fragment and named pKEX1M13.

The plasmid pUC12/URA3 (see example 12a), containing the URA3 gene cloned as HindIII fragment, is digested with HindIII to isolate the 1170 bp HindIII fragment [cf. Rose, M. et al. (1984) Gene 29, 115]. The sticky ends of the fragment are filled in with Klenow polymerase to create blunt ends. On the other hand, plasmid pKEX1M13 is linearized by endonuclease EcoRV digestion, whereby the KEX1 HindIII-BamHI fragment is cut, and dephosphorylated with alkaline phosphatase to avoid self-ligation. Then these two DNA fragments are mixed, ligated and transfected in E. coli strain JM103. The transformants are analysed by double digestion with HindIII and BamHI, where the size of the considerated HindIII-BamHI fragment increases from 1380 bp to 2550 bp. DNA of one correct clone is sequenced using the above described oligonucleotide as a sequencing primer to confirm the insertion of the URA3 fragment in the KEX1 gene at the position of the EcoRV cutting site. The plasmid is named pKEX1M13-URA3.

The pKEX1M13-URA3 DNA is digested with HindIII and BamHI to cut out the KEX1-URA3 hybrid fragment and without separation from the vector introduced into the S. cerevisiae strain H449 according to the above mentioned method (see Example 3). After the isolation of the membrane fraction from the Ura3⁺ transformants, the activity of yscα is measured using a chromogenic substrate (see Example 1). A single transformant, which shows no protease activity of yscα, is designated S. cerevisiae H449kex1.

EXAMPLE 15

Transformation of S. cerevisiae Strain H449kex1

Saccharomyces cerevisiae strain H449kex1 is transformed with plasmids
pDP34/PHO5(–173)-HIR
pDP34/GAPFL-HIR
pDP34/GAPEL-HIR
pDP34/PHO5(–173)-YHIR
pDP34/GAPFL-YHIR
pDP34/GAPEL-YHIR
pDP92/PHO5(–173)-YHIR
pDP92/GAPFL-YHIR
pDP92/GAPEL-YHIR
using the transformation protocol described by Hinnen et al. (supra). Transformed yeast cells are selected on yeast minimal medium plates supplemented with leucine but lacking uracil. Single transformed yeast cells are isolated and referred to as
Saccharomyces cerevisiae H449kex1/pDP34/PHO5(–173)-HIR
Saccharomyces cerevisiae H449kex1/pDP34/GAPFL-HIR
Saccharomyces cerevisiae H449kex1/pDP34/GAPEL-HIR
Saccharomyces cerevisiae H449kex1/pDP34/PHO5(–173)-YHIR
Saccharomyces cerevisiae H449kex1/pDP34/GAPFL-YHIR
Saccharomyces cerevisiae H449kex1/pDP34/GAPEL-YHIR
Saccharomyces cerevisiae H449kex1/pDP92/PHO5(–173)-YHIR
Saccharomyces cerevisiae H449kex1/pDP92/GAPFL-YHIR
Saccharomyces cerevisiae H449kex1/pDP92/GAPEL-YHIR

EXAMPLE 16

Fermentation of Transformed Yeast Strains on a Laboratory Scale

Cells of *Saccharomyces cerevisiae* H449kex1/pDP34/PHO5(−173)-YHIR and of *Saccharomyces cerevisiae* H449kex1/pDP34/GAPFL-YHIR are each grown in two subsequent precultures of 10 ml minimal medium composed of (g/l):

| | |
|---|---|
| Difco Yeast Nitrogen Base | 6.7 |
| asparagine | 10 |
| leucine | 1 |
| glucose | 20 |

The first preculture is grown for 60 h at 28° C. and 180 r.p.m. The second preculture is inoculated with 2% of the first preculture and incubated for 24 h at 28° C. and 180 r.p.m.

The main culture medium is composed of (g/l):

| | |
|---|---|
| yeast extract | 49 |
| glucose | 5 |
| fructose | 57 |
| NH$_4$NO$_3$ | 0.5 |
| MgSO$_4$ × 7 H$_2$O | 1.0 |
| CaCO$_3$ | 5.0 |
| Ca$_3$(PO$_4$)$_2$ | 2.0 |

The main culture is inoculated with about 2×10$^6$ cells/ml and incubated up to 72 h at 28° C. and 180 r.p.m. Approximately 1×10$^9$ cells/ml are obtained at the end of the fermentation. At several time points during the fermentation aliquots of the cultures are taken, the cells removed by centrifugation and the culture supernatant analysed for desulphatohirudin by HPLC (infra).

EXAMPLE 17
Production of Desulphatohirudin Variant HV1 on a 50 l Scale

A working cell bank of the two-micron free strain *Saccharomyces cerevisiae* H449kex1/pDP34/GAPFL-YHIR, has been used as a source of inoculum for the production of desulphatohirudin on a 50 l scale.

Ampoules of the working cell bank are preserved in the vapour phase in a liquid nitrogen container. The contents of one ampoule are used to inoculate a shake flask culture comprising a selective medium consisting of (g/l)

| | |
|---|---|
| yeast nitrogen base | 8.4 |
| L-asparagin monohydrate | 11.4 |
| L-histidin | 1.0 |
| L-leucine | 0.1 |
| D-glucose monohydrate | 20.0 |

The 500 ml flask contains 100 ml medium and is incubated for 48 h at 28° C. on an orbital shaker at a shaking speed of 180 rev/min.

The second shake flask pre-culture contains the same medium of which 600 ml are contained in a 2 l flask which has four baffles. The inoculum level from the first pre-culture is 5% (30 ml) and the flasks are incubated for 48 h at 28° C. on an orbital shaker at a speed of 120 rev/min.

A third pre-culture is fermented in a 50 l stainless steel bioreactor equipped with 4 baffles and a single disk turbine agitator with a diameter of 115 mm. The above medium is also used for this culture, the starting volume being 30 l. A single 2 l flask containing 600 ml culture is used to inoculate the 50 l reactor (2%). The fermentation lasts for about 42 h at a temperature of 28° C. The stirrer speed is 600 rev/min, aeration rate 1 vvm and the reactor is operated with an overpressure of 0.3 bar.

A similar 50 l bioreactor, additionally equipped for fed-batch processes, is used for the desulphatohirudin production stage. A medium consisting of (g/l)

| | |
|---|---|
| meat peptone (Merck) | 5.0 |
| yeast extract | 30.0 |
| ammonium sulphate | 6.0 |
| magnesium sulphate heptahydrate | 1.0 |
| sodium chloride | 0.1 |
| potassium dihydrogenphosphate | 1.0 |
| D-glucose monohydrate | 10.0 | is used for this stage (30 l). The inoculum level from the third preculture stage is optionally 2%. The fermentation lasts for 48 h at a temperature of 28° C. and the stirrer speed is set at 750 rev/min. The overpressure is initially set at 0.3 bar, but this can be raised to 1.0 bar during the course of the fermentation to maintain the dissolved oxygen tension above 20% saturation. The initial air flow is 0.25 vvm but this is increased to 1 vvm after nine hours in order to ensure an adequate oxygen supply.

The pH value falls during the early part of the fermentation to a value of 5.0 at which it is maintained by an automatic feed of ammonium hydroxide.

In simple batch culture the biomass level attained, and consequently the desulphatohirudin titre, is dependent upon the amount of the carbon source which is batched into the fermenter at the beginning. This in turn is dictated by the oxygen transfer capacity of the bioreactor and the need to avoid excessive production of ethanol by the growing yeast. These limitations can be overcome by using fed-batch technology. Thus rather little glucose is included in the start medium but a feed of glucose is made to support a considerably higher final biomass concentration and a desulphatohirudin titre approximately three times that reached in batch culture. In practice the feed is increased at intervals in a stepwise manner to a final feed rate of 175 g/h of glucose monohydrate.

Small additions of a silicone based antifoam are used to control foaming when necessary. A portion of the exit gas from the fermenter is analysed to provide information about the oxygen uptake and carbon dioxide evolution rate. The dissolved oxygen tension is measured on-line using a sterilizable electrode.

Samples are withdrawn at 6 hourly intervals throughout the process to allow monitoring of the glucose and ethanol concentrations, the desulphatohirudin titre by bio-assay and HPLC, and also to check the sterility. As evidenced by HPLC the produced desulphatohirudin is essentially free of C-terminally shortened analogs. At the end of the fermentation process desulphatohirudin can be recovered from the culture supernatant.

EXAMPLE 18
Recovery of desulphatohirudin from *S. cerevisiae* cultured on a 50 l scale The culture broth (see Example 17) is mixed with Amberlite XAD-7 and is subjected to adsorption for about 4 hours at 25° C. The cells are separated from the resin in a column. After washing with 1M NaCl the resin is eluted with Tris buffer (50 mM, pH 7.0–8.5). The main fraction (30 l) is adjusted to pH 2.9 and is applied to a S-Sepharose column (Amicon PA, equilibrated with ammonium formiate buffer 25 mM, pH 2.9) having a bed volume of 2 l. After washing with ammonium formiate buffer (40 mM, pH 3.6) elution is done with ammonium formiate buffer (50 mM, pH 3.8). The main eluate fraction (10 l) is concentrated by means of a Filtron Minisette ultrafiltration system equipped with a Ω 3 k membrane. A 0.5 l aliquot of the resulting clear protein solution is applied to a Bio-Gel P-6 fine column (Amicon GF equilibrated with 0.5% acetic acid) having a bed volume of 1.5 l. Elution is done with 0.5% acetic acid. The main eluate fraction (1 l) is concentrated by means of ultrafiltration and subsequently applied to a Q-Sepharose fast flow column (Amicon PA, equilibrated with ammonium formiate buffer 25 mM, pH 2.9) having a bed volume of 2 l. Elution is done with ammonium formiate buffer (50 mM, pH 4.2). The main eluate fraction is concentrated by means of ultrafiltration and is subsequently diafiltrated against water. The resulting clear aqueous solution is lyophilised. The solid consists of pure desulphatohirudin which is free of detectable amounts of C-terminally shortened analogs.

EXAMPLE 19
Disruption of the PRA1 gene in S. cerevisiae H 449

S. cerevisiae strain H 449 (DSM 4413; prb, leu2, ura3, cir°) is made multiple-protease deficient by means of gene disruption. Gene disruption as compared to meiotic crosses has the advantage of stably introducing a mutation while keeping the genetic background of a given strain identical.

In a first step, proteinase yscA activity is eliminated via disruption of the PRA1 gene [Ammerer, G. et al. (1986) Mol. Cell. Biol. 6, 2490]. PRA1 is isolated from total genomic yeast DNA, digested with SacI and PstI. 2 kb fragments are isolated from a preparative 0.6% agarose gel, electroeluted and ligated into the PstI-SacI sites of the polylinker region of pUC19. The vector is transformed into E. coli JM 109 and 280 individual colonies are picked. The colonies are individually grown in wells of microtiter plates containing LB +amp medium. Colony hybridization is carried out essentially as described [Woods, D. E. et al. (1982) Proc. Natl. Acad. Sci. USA 79, 5651] with the following $^{32}$P-labelled oligonucleotide probe

5'-AAGCCTAGTGACCTAGT-3' which is derived from the published PRA1 sequence [Ammerer et al. supra]. 3 positive clones are picked, DNA of one—pUC19/PRA1—is cut with SacI and XhoI and the 1.9 kb fragment containing the entire PRA1 gene subcloned into the KS polylinker region of the Bluescript vector M13+ (Stratagene Cloning Systems, San Diego, Calif., USA). A 1.2 kb HindIII fragment containing the entire URA3 gene [Rose, M. et al. (1984) Gene 29, 113]) is inserted into the unique HindIII site within the coding region of the PRA1-insert. The resulting plasmid is designated M13+/pra1::URA3. M13+/pra1::URA3 is digested with SacI/XhoI and the 3.1 kb fragment without separation from the vector used to transform S. cerevisiae H 449 as described (see Example 3). Uracil independent transformants are picked, DNA prepared and SacI/XhoI digested and checked for correct PRA1 gene disruption by Southern blotting. One transformant with the correct shift of the SacI/XhoI fragment hybridizing with PRA1 from 1.9 kb to 3.1 kb is designated Tr 1186.

In the next step Tr 1186—with the disruption in its PRA1 gene by pra1::URA3—is again made uracil dependent by introducing a deletion in the pra1::URA3 gene insert. Tr 1186 is transformed with 1 µg of plasmid YEp13 [Broach, J. R. et al. (1979) Gene 8, 121) together with 10 µg of plasmid pUC12ura3delta containing a 200 bp deletion in the URA3 gene [Sengstag, C. et al. (1978) Nucleic Acids Research 15, 233]). 3000 leucine prototrophic yeast transformants are resuspended in 5 ml minimal medium (Difco yeast nitrogen base without aminoacids to which 2% glucose, 0.1% leucine, 0.1% uracil and 0.25% fluoroorotic acid are added) in a small shake flask and incubated for 60 hours at 30° C. and 180 rpm. Transformants which grow are resistant to the toxic analogue fluoroorotic acid and carry therefore a replacement in the pra1::URA3 region by ura3delta. The grown cells are plated out on full medium composed of (g/l): Peptone 20, yeast extract 10, glucose 20 and after growth for 48 hours at 30° C. replica-plated onto minimal medium (Difco yeast nitrogen base without amino acids, supplemented with 2% glucose and 0.1% leucine) to detect uracil auxotrophs. Several auxotrophs are picked and tested for plasmid YEp13 loss conferring leucine auxotrophy. One individual colony—designated Tr 1195—requiring leucine and uracil is picked and used for further experimentation.

EXAMPLE 20
Disruption of the PRC1 Gene in Tr 1195

Next, carboxypeptidase yscY activity in Tr 1195 is eliminated. PRC1 coding for yscY [Rothman, J. H. et al. (1986) Proc. Natl. Acad. Sci. USA 83, 3248] is isolated from the yeast genomic library in the centromer vector pCS19 [Sengstag, C. et al. (1978) Nucleic Acids Research 15, 233] by colony hybridization with 2 synthetic oligonucleotides 5'-GAAAGCATTCACCAGTTTACTATGTGG-3' and

5'-CGAATGGATCCCAACGGGTTTCTCC-3' corresponding to the 5' and 3' end of the PRC1 coding sequence. One positive clone is designated as pCS19/cpy8. pCS19/cpy8 DNA is digested with ClaI/PvuII, loaded on a 0.6% preparative agarose gel and a 2.6 kb fragment is isolated and electroeluted. This ClaI/PvuII fragment, containing the entire PRC1 gene, is further subcloned into the NarI/SmaI sites of pUC19. The resulting plasmid pUC19/PRC1 is cut at the unique StuI site, into which the 1.2 kb URA3 fragment (see Example 19) is ligated. For this purpose, the sticky HindIII ends of the URA3 containing fragment are filled in a reaction with Klenow DNA polymerase to fit into the blunt-ended StuI-site of pUC/PRC1.

The resulting plasmid pUC19/prc::URA3 is digested with AatII and the AatII fragment without separation from the vector used to transform S. cerevisiae Tr 1195 as described. One uracil independent transformant—Tr 1206—is tested for correct PRC1 gene disruption by Southern blotting and afterwards again made uracil dependent as described (see Example 19). The resulting S. cerevisiae strain is designated Tr 1210 (pra1, prb1, prc1, ura3, leu2, cir°).

EXAMPLE 21
Preparation of a kex1 Variant of S. cerevisiae Tr 1210

Carboxypeptidase yscα activity is eliminated from S. cerevisiae strain Tr 1210 by disruption of the genomic KEX1 gene as described (see Example 14). The resulting S. cerevisiae strain, which shows no protease activity of yscα, is designated Tr 1302 (pra1, prb1, prc1, ura3, leu2, cir°, kex1).

EXAMPLE 22
Construction of Hirudin Mutants HV1-KR, HV1-SFRY, HV1-WQLR

In order to further evaluate yscα-mediated C-terminal degradation of heterologous proteins with different C-terminal amino acids, hirudin mutants are created different in their C-terminal amino acid composition. As a general method, site-directed in vitro mutagenesis is used, in principle as described [Bio-Rad Huta-Gene M13 kit, Bio-Rad, Richmond, Calif. USA].

The following mutants are constructed:
1. HV1-KR, corresponding to [Lys$^{64}$-Arg$^{65}$]hirudin variant 1
2. HV1-SFRY, corresponding to [Ser$^{62}$-Phe$^{63}$-Arg$^{64}$-Tyr$^{65}$]HV1
3. HV1-WQLR, corresponding to [Trp$^{62}$-Glu$^{63}$-Leu$^{64}$-Arg$^{65}$]HV1.

The amino acid sequences of all hirudin mutants correspond to that of hirudin variant 1 up to amino acid 61 or 63, respectively.

In HV1-SFRY the C-terminus is identical to atrial natriuretic peptide [Vlasuk et al. (1986) J. Biol. Chem. 261, 4789–4796] and in HV1-WQLR the C-terminus corresponds to epidermal growth factor [George-Nascimento, C. et al. (1988) Biochemistry 27, 797–802], both of which are known to be C-terminally degraded by protease-containing wild-type yeast strains.

In a first step, plasmid pJDB207/GAPFL-HIR (as disclosed in European Patent Application No. 225633) is digested with SalI-HindIII, giving a 1.2 kb fragment containing the full-length hirudin expression cassette. The 1.2 kb SalI-HindIII fragment is subcloned into SalI-HindIII cut Bluescript M13+ with the SK polylinker. The resulting plasmid M13+/HV1 is transfected into *E. coli* CJ 236 in order to incorporate uracil as described (Bio-Rad Muta-Gene M13 kit supra). Single-stranded DNA from transfected *E. coli* CJ 236 is isolated using M13 helper phage (Stratagene supra).

In order to construct HV1-KR the mutagenic primer
5'-CCGGAAGAATACAAGAGGTAGGATCCT-3' is used.
For HV1-SFRY the mutagenic primer
5'-GAAGAAATCCCGGAATCTTTCAGATACTAG GATCCTGGTACG-3' is used.
For HV1-WQLR the mutagenic primer
5'-GAAGAAATCCCGGAATGGGAACTGAGATAG GATCCTGGTACG-3' is used.

200 pmoles of each primer are first phosphorylated in a total volume of 30 µl containing 3 µl 1 M Tris-HCl pH 8.0, 0.3 µl 1 M MgCl$_2$, 0.75 µl 0.2 M DTT, 0.6 µl 20 mM ATP. 4.5 units T4 polynucleotide kinase are added and the mixture incubated at 37° C. for 45 min and at 65° C. for 10 min.

The phosphorylated oligonucleotides are then annealed to the template DNA under the following conditions: 0.1 pmoles of uracil containing DNA derived from M13+/HV1 are incubated with 2 pmoles of phosphorylated primer each in a total volume of 10 µl annealing buffer (20 mM Tris-HCl pH 7.4, 2 mM MgCl$_2$, 50 mM NaCl). The mixtures are heated in a water bath to 80° C. and then allowed to cool slowly until ambient temperature is reached.

Complementary strands are then formed under the following conditions: 10 µl of each of the annealing mixtures are incubated with 4 µl 2 mM dNTP's, 0.75 µl 20 mM ATP, 0.75 µl 0.5 M Tris-HCl pH 7.4, 0.75 µl 0.1 M MgCl$_2$, 2.15 µl 0.2 M DTT, 1 unit T4 DNA polymerase and 2 units T4 DNA ligase. The reaction mixtures are first incubated on ice for 5 min, then at 25° C. for 5 min and finally at 37° C. for 90 min. The resulting double-stranded DNA's are transformed into *E. coli* JM 101, a strain which efficiently removes the uracil-containing template, leaving the mutagenized complementary strand to replicate (Bio-Rad supra). Plasmids are prepared and checked for absence of the PstI site which should only be present in the last 2 codons of unmutagenized wild-type HV1 DNA.

Correct mutagenesis is further confirmed by sequencing the new hirudin mutants using the following primer:
5'-GAAGGTACCCCGAAACCGCA-3' which corresponds to the hirudin coding sequence about 20 bp upstream of the mutagenic primers.

Finally the three mutagenized SalI-HindIII fragments are excised from Bluescript M13+ and religated into the SalI-HindIII sites on pJDB207.

The three new plasmids are designated
1. pJDB207/GAPFL-HV1-KR
2. pJDB207/GAPFL-HV1-SFRY
3. pJDB207/GAPFL-HV1-WQLR Alternatively, and in order to be able to transform cir° strains such as Tr 1302 (supra, see Example 21) the hirudin mutants are subcloned into the full 2 micron vector pDP34 (see Example 9, supra). pDP34 is cut at the unique BamH1 site and the sticky ends filled in with Klenow DNA polymerase to create blunt ends. The SalI-HindIII fragments from Bluescript M13+ encoding the mutated hirudin sequences (supra) are also made blund-ended and ligated into the blunt-ended (BamH1) site of pDP34. The resulting plasmids are designated
1. pDP34/GAPFL-HV1-KR
2. pDP34/GAPFL-HV1-SFRY
3. pDP34/GAPFL-HV1-WQLR

EXAMPLE 23

Transformation of *S. cerevisiae* Strains BYSKEX1 and BYSkex1with pJDB207/GAPFL-HIR, pJDB207/GAPFL-HV1-KR, pJDB207/GAPFL-HV1-SFRY and pJDB207/GAPFL-HV1-WQLR and of *S. cerevisiae* Strains Tr1210 and Tr1302 with pDP34/GAPFL-HV1-KR, pDP34/GAPFL-HV1-SFRY and pDP34/GAPFL-HV1-WQLR pJDB207/GAPFL-HV1-KR, pJDB207/GAPFL-HV1-SFRY, pJDB207/GAPFL-HV1-WQLR and pJDB207/GAPFL-HIR are transformed into *S. cerevisae* BYSKEX1 (=DSM 4583) and BYSkex1 using the standard protocol and leucine selection (see Example 3). In the same way pDP34/GAPFL-HV1-KR, pDP34/GAPFL-HV1-SFRY and pDP34/GAPFL-HV1-WQLR are transformed into *S. cerevisiae* strains Tr1210 and Tr1302.

The resulting strains are designated
*S. cerevisiae* BYSKEX1/pJDB207/GAPFL-HIR
*S. cerevisiae* BYSKEX1/pJDB207/GAPFL-HV1-KR
*S. cerevisiae* BYSKEX1/pJDB207/GAPFL-HV1-SFRY
*S. cerevisiae* BYSKEX1/pJDB207/GAPFL-HV1-WQLR
*S. cerevisiae* BYSkex1/pJDB207/GAPFL-HIR
*S. cerevisiae* BYSkex1/pJDB207/GAPFL-HV1-KR
*S. cerevisiae* BYSkex1/pJDB207/GAPFL-HV1-SFRY
*S. cerevisiae* BYSkex1/pJDB207/GAPFL-HV1-WQLR
*S. cerevisiae* Tr1210/pDP34/GAPFL-HV1-KR
*S. cerevisiae* Tr1210/pDP34/GAPFL-HV1-SFRY
*S. cerevisiae* Tr1210/pDP34/GAPFL-HV1-WQLR
*S. cerevisiae* Tr1302/pDP34/GAPFL-HV1-KR
*S. cerevisiae* Tr1302/pDP34/GAPFL-HV1-SFRY
*S. cerevisiae* Tr1302/pDP34/GAPFL-HV1-WQLR Fermentation of the *S. cerevisiae* strains is carried out in minimal medium (pre- and main culture) as described (see Example 17).

EXAMPLE 24

Analytics of Hirudin Variant HV1 and its Mutants from Fermentation Cultures of *Saccharomyces cerevisiae* Transformants BYSkex1 and BYSKEX1 Using Reversed Phase HPLC After 72 hours of fermentation samples from liquid yeast cultures are prepared by centrifugation to produce a clear solution which is diluted 1:10 with acetic acid (1M) and are subjected to HPLC analysis under following conditions.

A HIBAR (MERCK) column (4×125 mm) is filled with reversed phase, spherical silica material MACHEREY-NAGEL), a spherical stationary phase with a particle diameter of 5 μm and a porosity of 100 A. The column endings are equipped with stainless steel frits. Mobile phase A is made from water (Nanopure®, BARNSTEAD) containing 0.1% (v/v) trifluoroacetic acid. Mobile phase B is made from 20% of mobile phase A and 80% (v/v) of acetonitrile (HPLC-grade, FLUKA) containing 0.075% (v/v) of trifluoroacetic acid.

Chromatographic separations are performed at a flow rate of 1.5 ml/min running the following gradient and the eluents are monitored by absorbance at 216 nm.

| t(min) | % A | % B |
|--------|-----|-----|
| 0      | 90  | 10  |
| 1      | 79  | 21  |
| 9      | 79  | 21  |
| 17     | 64  | 36  |
| 20     | 0   | 100 |
| 22     | 0   | 100 |
| 24     | 90  | 10  |
| 32/0   | 90  | 10  |

A standard solution for the calibration of the system is made by dissolving 1 mg of pure desulphatohirudin in 1 ml water. 50 μl of this standard solution are injected onto the column and chromatographed as described to calibrate the system.

FIG. 8 shows the results which indicate that S. cerevisiae BYSkex1 produces full-lengths hirudins (either hirudin HV1 wild-type or the mutants HV1-KR, HV1-SFRY, HV1-WQLR) with different retention times than hirudin degradation products produced by S. cerevisiae BYSKEX1. Wild-type hirudin HV-1 shows the typical mixture of full-length HV-1 (retention time 17.05 min) and the two degradation products "HIR-64" (ret. time 17.8 min) and "HIR-63" (ret. time 15.33 min) in BYSKEX1. BYSkex1 produces only "HIR-65" (ret. time 17.05 min). In case of the mutant HV1-KR BYSKEX1 produces exclusively the degradation product with two C-terminal amino acids lacking (="HIR-63", ret. time 15.9 min), whereas BYSkex1 produces full-length HV1-KR (ret. time 14.4 min).

In case of the mutant HV1-WQLR BYSKEX1 shows the degradation product with a retention time of 18.6 min, BYSkex1 produces predomantly full-length HV1-WQLR (ret. time 17.3 min) and only traces of the degradation product. HV1-SFRY in full-length is found only in traces (ret. time 17.1 min) in BYSkex1 shows only intact HV1-SFRY (ret. time 17.1 min). The large peak (ret. time 15.7 min) is unrelated to HV1-SFRY.

Analogous results are obtained when the KEX1 S. cerevisiae strains Tr1210/pDP34/GAPFL-HV1-KR, Tr1210/pDP34/GAPFL-HV1-SFRY and Tr1210/pDP34/GAPFL-HV1-WQLR are compared with the corresponding kex1 strains Tr1302/pDP34/GAPFL-HV1-KR, Tr1302/pDP34/GAPFL-HV1-SFRY and Tr1302/pDP34/GAPFL-HV1-WQLR.

Deposition of microorganisms

The following microorganism strains were deposited at the Deutsche Sammlung von Mikroorganismen (DSM), Mascheroder Weg 1b, D-3300 Braunschweig (deposition dates and accession numbers given):

*Saccharomyces cerevisiae* H449: Feb. 18, 1988, DSM 4413;
*Escherichia coli* JM109/pDP38: Feb. 19, 1988, DSM 4414;
*Escherichia coli* JM109/pDP34: Mar. 14, 1988, DSM 4473.
*Saccharomyces cerevisiae* BYS232-31-42: May 6, 1988, DSM 4583.

What is claimed is:

1. A *Saccharomyces cerevisiae* strain which lacks carboxypeptidase yscα activity and lacks proteolytic activity selected from the group consisting of proteolytic yscA, yscB, yscY and yscS activity and has been transformed with a hybrid vector comprising a *Saccharomyces cerevisiae* promoter operably linked to a DNA coding for a full-length mature protein which bears no basic C-terminal amino acids and which is selected from the group consisting of hANP, EGF, connective tissue activating peptide-III and desulphatohirudin.

2. A method for the production of a *Saccharomyces cerevisiae* strain which lacks carboxypeptidase yscα activity and lacks proteolytic activity selected from the group consisting of proteolytic yscA, yscB, yscY and yscS activity and has been transformed with a hybrid vector comprising a *Saccharomyces cerevisiae* promoter operably linked to a DNA coding for a full-length mature protein which bears no basic C-terminal amino acids and which is selected from the group consisting of hANP, EGF, connective tissue activating peptide-III and desulphatohirudin, comprising transforming a *Saccharomyces cerevisiae* strain which lacks carboxypeptidase yscα activity and lacks proteolytic activity selected from the group consisting of proteolytic yscA, yscb, yscY and yscS activity with said hybrid vector.

3. A method for the production of a full-length mature protein which bears no basic C-terminal amino acids and which is selected from the group consisting of hANP, EGF, connective tissue activating peptide-III and desulphatohirudin, comprising culturing a *Saccharomyces cerevisiae* strain which lacks carboxypeptidase yscα activity and lacks proteolytic activity selected from the group consisting of proteolytic yscA, yscB, yscY and yscS activity and has been transformed with a hybrid vector comprising a *Saccharomyces cerevisiae* promoter operably linked to a DNA coding for said protein, and isolating said protein.

4. A *Saccharomyces cerevisiae* strain according to claim 1, wherein said hybrid vector comprises a *Saccharomyces cerevisiae* promoter operably linked to a first DNA encoding a signal peptide linked in a proper reading frame to a second DNA encoding said full-length mature protein and a DNA containing *Saccharomyces cerevisiae* transcription termination signals.

5. A *Saccharomyces cerevisiae* strain according to claim 1, wherein said full-length mature protein is desulphatohirudin.

6. A *Saccharomyces cerevisiae* strain according to claim 1, which is free of endogenous two-micron plasmid and has been transformed with a hybrid vector comprising the complete two-micron DNA comprising intact REP1, REP2 and FLP genes and intact ORI, STB, IR1 AND IR2 sites.

7. A *Saccharomyces cerevisiae* strain according to claim 1, wherein said hybrid vector comprises a *Saccharomyces cerevisiae* promoter selected from the group consisting of the MFα1 promoter, GAL1 promoter, a promoter of a gene encoding a glycolytic enzyme, ADHI promoter, TRPI promoter, PHO5 and the PHO5 promoter in which the upstream activation sites have been deleted.

8. A *Saccharomyces cerevisiae* strain according to claim 4, wherein said hybrid vector comprises a first DNA selected from the group consisting of the hirudin signal sequence, the signal and prepro sequences of the yeast invertase, α-factor pheromone peptidase (KEX1), "Killer toxin" and repressible acid phosphatase (PHO5) genes, and the glucoamylase signal sequence from *Aspergillus awamori*.

9. A method for the production of an essentially homogeneous mature protein according to claim 3, wherein said hybrid vector comprises a *Saccharomyces cerevisiae* promoter operably linked to a first DNA encoding a signal peptide linked in the proper reading frame to a second DNA coding for said protein and a DNA sequence containing *Saccharomyces cerevisiae* transcription termination signals.

10. A method for the production of an essentially homogenous mature protein according to claim 9, wherein said protein is desulphatohirudin.

11. A method according to claim 10 for the preparation of desulphatohirudin variant HV1.

* * * * *